(12) United States Patent
Medin et al.

(10) Patent No.: US 10,597,704 B2
(45) Date of Patent: Mar. 24, 2020

(54) NUCLEIC ACID CLASSIFICATION

(71) Applicant: Bio-NEMS Corporation, Mountain View, CA (US)

(72) Inventors: David Lawrence Medin, Mountain View, CA (US); Sherwood Russ Lehrman, Los Altos, CA (US)

(73) Assignee: Bio-NEMS Corporation, Mountain View, CA (US)

( * ) Notice: Subject to any disclaimer, the term of this patent is extended or adjusted under 35 U.S.C. 154(b) by 0 days.

(21) Appl. No.: 16/400,839

(22) Filed: May 1, 2019

(65) Prior Publication Data

US 2019/0316186 A1 Oct. 17, 2019

Related U.S. Application Data

(63) Continuation of application No. 15/585,691, filed on May 3, 2017, now abandoned, which is a continuation of application No. 13/969,241, filed on Aug. 16, 2013, now abandoned.

(60) Provisional application No. 61/684,551, filed on Aug. 17, 2012.

(51) Int. Cl.
*C12Q 1/6827* (2018.01)
(52) U.S. Cl.
CPC ................. *C12Q 1/6827* (2013.01)
(58) Field of Classification Search
None
See application file for complete search history.

(56) References Cited

U.S. PATENT DOCUMENTS

| | | |
|---|---|---|
| 2002/0146706 A1 | 10/2002 | Bader et al. |
| 2003/0027149 A1 | 2/2003 | Dorris et al. |
| 2005/0079501 A1 | 4/2005 | Koike et al. |
| 2005/0164236 A1 | 7/2005 | Su et al. |
| 2009/0042280 A1 | 2/2009 | Yang et al. |
| 2011/0039720 A1 | 2/2011 | Vossenaar et al. |

(Continued)

FOREIGN PATENT DOCUMENTS

| | | |
|---|---|---|
| CN | 102482719 A | 5/2012 |
| JP | 3853845 B2 | 12/2006 |
| WO | WO2006081353 | 8/2006 |

(Continued)

OTHER PUBLICATIONS

Ming Su et al., "Microcantilever resonance-basd DNA detection with nanoparticle probes," Applied Physics Letters, vol. 82, No. 20, May 19, 2003, pp. 3562-3564.

(Continued)

*Primary Examiner* — Kaijiang Zhang
(74) *Attorney, Agent, or Firm* — Fish & Richardson P.C.

(57) ABSTRACT

A method and system for classifying a target nucleic acid includes exposing, in a test system, one or more capture probes to the target nucleic acid. The one or more capture probes is attached to a surface. A first hybridization condition is established in the test system. A first degree of hybridization of the one or more capture probes with the target nucleic acid under the first hybridization condition is determined. A second hybridization condition in the test system is established. A second degree of hybridization of the one or more capture probes with the target nucleic acid under the second hybridization condition is determined and the target nucleic acid is classified by comparing the first and the second degrees of hybridization.

15 Claims, 16 Drawing Sheets

(56) References Cited

U.S. PATENT DOCUMENTS

2014/0051596 A1    2/2014  Medin et al.
2018/0057865 A1    3/2018  Medin et al.

FOREIGN PATENT DOCUMENTS

WO    WO2009014830    1/2009
WO    WO2009046110    4/2009

OTHER PUBLICATIONS

Kim, Seung Beom, International Search Report and Written Opinion of International Application No. PCT/US2013/055425, dated Nov. 18, 2013, 11 pages.

Linder, Nora, International Preliminary Report on Patentability, International Application No. PCT/US2013/055425, dated Feb. 17, 2015, 6 pages.

Nasef et al., "Electrochemical melting-curve analysis," Electrochem. Commun. 2010, 12:1030-1033.

Qavi et al., "Isothermal Discrimination of Single-Nucleotide Polymorphisms via Real-Time Kinetic Desorption and Label-Free Detection of DNA Using Silicon Photonic Microring Resonator Arrays," Anal. Chem. 2011, 83:6827-6833, published Aug. 11, 2011.

Qavi et al., "Anti-DNA:RNA Antibodies and Silicon Photonic Microring Resonators: Increased Sensitivity for Multiplexed microRNA Detection," Anal. Chem. 2011, 83:5949-5956, published Jun. 29, 2011.

Supplementary Partial European Search Report for Application No. EP 13 82 9944, dated Feb. 2, 2016, 6 pages.

NUCLEIC ACID CLASSIFICATION

CROSS-REFERENCE TO RELATED APPLICATIONS

This application is a continuation application of and claims priority to U.S. application Ser. No. 15/585,691, filed on May 3, 2017, which is a continuation of and claims priority to U.S. application Ser. No. 13/969,241, filed on Aug. 16, 2013, which claims priority to U.S. Provisional Application Ser. No. 61/684,551, filed Aug. 17, 2012, the entire contents of which are hereby incorporated by reference.

TECHNICAL FIELD

This disclosure relates generally to electronics and more particularly to the identification of nucleic acids and other biologically relevant macromolecules.

BACKGROUND

Identification of nucleic acids can be useful for several applications, including analysis of gene expression, genome analysis for clinical diagnosis, biomedical research, forensic investigations, and biometrics. In a conventional approach, one assay format is based on hybridization of target nucleic acids that are fluorescently-labeled with complementary probes that are bound to a solid surface. For example, using a set of 14 to 40 complementary probes, each probe containing 25 nucleotides, it is possible to classify single nucleotide polymorphisms (SNPs).

Another conventional approach for classifying nucleic acids is based on divergent sequences. For example, the classifying nucleic acids can include hybridization of target nucleic acid with capture probes on particulates. The hybrid can include an oligonucleotide sequence that is immediately adjacent to a polymorphic site. The hybrid can be extended by polymerase to incorporate the nucleotide that appropriately pairs with the polymorphic nucleotide. The incorporation of the nucleotide results in chain termination. The compound is marked with a fluorescent label and spectral analysis can provide the identity of the nucleotide.

Long, closely related alleles appear in human genomic DNA. The ability of conventional approaches to distinguish variants of long, closely related genetic sequences that contain short tandem repeats (STRs) that vary in length is limited. Conventional approaches of nucleic acid identification often require long equilibration times, and are limited by high background signal and low dynamic range.

SUMMARY

Nucleic acids can be identified by monitoring hybridization in different conditions on microarray surfaces. In a first aspect, a method for classifying a target nucleic acid can include exposing, in a test system, one or more capture probes to the target nucleic acid, the one or more capture probes being attached to a surface, establishing a first hybridization condition in the test system, determining a first degree of hybridization of the one or more capture probes with the target nucleic acid under the first hybridization condition, establishing a second hybridization condition in the test system, determining a second degree of hybridization of the one or more capture probes with the target nucleic acid under the second hybridization condition, and classifying the target nucleic acid by comparing the first and the second degrees of hybridization.

In some implementations, the test system can include one or more sensors on the surface configured to measure hybridization of the one or more capture probes with the target nucleic acid. The sensor can be a resonator array configured to measure a mass of an object on at least one surface of the resonator array. One or more captures probes can be attached to the surface of the resonator system. Determining the first and second degrees of hybridization of the one or more capture probes with the target nucleic acid can include measuring the mass on the surface of the resonator array.

In another aspect, exposing the one or more capture probes to the target nucleic acid includes contacting the one or more capture probes with a solution containing the target nucleic acid. Establishing the first hybridization condition can include adjusting a temperature of the solution to a first temperature and establishing the second hybridization condition includes adjusting the temperature of the solution to a second temperature.

In some implementations, the first hybridization condition can be selected to minimize hybridization between a target nucleic acid and the one or more capture probes, and the second hybridization condition can be selected to favor hybridization between the target nucleic acid and the one or more capture probes. Classifying the target nucleic acid can include progressively adjusting one or more hybridization conditions of the test system to favor hybridization between a target nucleic acid and one or more capture probes. After each adjustment, a degree of hybridization of the one or more capture probes with the target nucleic acid can be determined and the hybridization conditions can be continuously adjusted until the degree of hybridization reaches a threshold degree of hybridization.

In some implementations, the test system can include one or more first capture probes at a first location and one or more second capture probes at a second location. Classifying the target nucleic acid can include progressively adjusting one or more hybridization conditions of the test system. After each adjustment, a respective degree of hybridization for each of the first and second locations, can be determined and it can be determined whether the degree of hybridization at the first location reaches a threshold degree of hybridization prior to or after the degree of hybridization at the second location reaches the threshold degree of hybridization.

In another general aspect, the method can include calibrating the test system prior to exposing the one or more capture probes to the target nucleic acid, including attaching one or more double stranded nucleic acid capture probes to a surface of the test system, contacting the one or more double stranded nucleic acid capture probes with a solution, progressively adjusting one or more hybridization conditions of the test system until a degree of dissociation of the double stranded nucleic acid capture probes is reached, so that the solution contains single stranded nucleic acid and single stranded nucleic acid capture probes remain on the surface, recording the one or more hybridization conditions at which the degree of dissociation of a first double stranded nucleic acid capture probes is reached, generating a single stranded nucleic acid, and removing the single stranded nucleic acid from the test system.

In some implementations, the method can further include calibrating the test system prior to exposing the one or more capture probes to the target nucleic acid, including measuring a first set of nucleic acid capture probes attached to the surface of the test system, progressively adjusting the one or more hybridization conditions of the test system until the recorded hybridization condition is passed, measuring a second set of nucleic acid capture probes attached to the surface of the test system, and determining changes to the single stranded nucleic acid capture probes based on the first set of nucleic acid capture probes and the second set of nucleic acid capture probes.

In another general aspect, the method for determining an optimal density of capture probes can include classifying a target nucleic acid, determining the optimal density of capture probes on a test system. Determining can include exposing, in a test system, at a hybridization condition, a first set of capture probes to the target nucleic acid, the first set of capture probes being attached to a first surface, determining a first association rate at the first surface, exposing, in the test system, at the hybridization condition, a second set of capture probes to the target nucleic acid, the second set of capture probes being attached to a second surface and having a density different from first set of capture probes at the first surface, determining a second association rate at the second surface, and comparing the first association rate with the second association rate.

In some implementations, the optimal density of capture probes can be related to a sequence length of the capture probe. The test system can include a plurality of attachment surfaces, each of the plurality of attachment surfaces including a plurality of capture probes. Each of the plurality of capture probes, included by one of the plurality of attachment surfaces, can include an identical sequence.

In some implementations, the first of the plurality of attachment surfaces can include a first plurality of capture probes. A second of the plurality of attachment surfaces can include a second plurality of capture probes different from the first plurality of capture probes, the first and the second of the plurality of attachment surfaces can have different optimal densities of capture probes.

In another general aspect, a test system for classifying a target nucleic acid can include: one or more capture probes, a detector configured to determine a degree of hybridization of the one or more capture probes with the target nucleic acid, and a non-transitory computer readable medium. The non-transitory computer readable medium can store instructions that, when executed by a control system, causes the control system to perform a plurality of operations. The operations can include: establishing a first hybridization condition in the test system, determining, uses the detector, a first degree of hybridization of the one or more capture probes with the target nucleic acid under the first hybridization condition, establishing a second hybridization condition in the test system, determining, using the detector, a second degree of hybridization of the one or more capture probes with the target nucleic acid under the second hybridization condition and classifying the target nucleic acid by comparing the first and the second degrees of hybridization.

In some implementations, the detector can include a resonator array. Exposing the one or more capture probes to the target nucleic acid can include contacting the one or more capture probes with a solution containing the target nucleic acid, establishing the first hybridization condition includes adjusting a temperature of the solution to a first temperature and establishing the second hybridization condition can include adjusting the temperature of the solution to a second temperature.

In some implementations, the first hybridization condition can be selected to reduce hybridization between a target nucleic acid and the one or more capture probes, and the second hybridization condition can be selected to favor hybridization between the target nucleic acid and the one or more capture probes. The control system can include a processor and a conditioning system configured to adjust one or more hybridization conditions in the test system. The conditioning system includes a heating element or a cooling element or both.

In another general aspect, a method for classifying a target nucleic acid can include: exposing, in a test system, one or more capture probes to the target nucleic acid, the one or more capture probes being attached to a detector, measuring a first mass of the target nucleic acid hybridized with the one or more capture probes, modifying the target nucleic acid to generate a second mass, measuring the second mass of the target nucleic acid hybridized with the one or more capture probes, and classifying the target nucleic acid based on comparing the first mass with the second mass. The second mass can be substantially larger than the first mass. The detector can include an oscillating resonator array.

In some implementations, modifying can include adding a mass reporter to the target nucleic acid. Modifying can include a covalent bond and/or a non-covalent bond. The modified target nucleic acid can include one or more unpaired regions configured to modify the target nucleic acid for generating a third mass. The one or more unpaired regions can include biotin binding sites.

In another general aspect, a method for performing sequence analysis on a target nucleic acid, the method comprising: exposing, in a test system, the target nucleic acid to a polymerase that includes a target nucleotide targeted to a target nucleobase on the target nucleic acid, the target nucleic acid being attached to a surface; and determining a mass shift of the target nucleic acid resulting from the exposure of the target nucleic acid to the polymerase.

In some implementations, the method further comprises determining, based on the mass shift, a characteristic of the target nucleic acid regarding the target nucleobase. Determining the characteristic comprises determining a position of the target nucleobase in the target nucleic acid or a number of positions occupied by the target nucleobase in the target nucleic acid. The test system comprises a resonator array configured to measure a mass of an object on the surface; and determining the mass shift comprises measuring the mass of the target nucleic acid on the surface prior to exposing the target nucleic acid to the polymerase and measuring the mass of the target nucleic acid on the surface after exposing the target nucleic acid to the polymerase and determining a difference between the two measured masses. The target nucleotide is targeted to the target nucleobase by being configured to optimally hybridize with the target nucleobase. The target nucleotide includes a functional group that reversibly reduces growth of the target nucleic acid. Exposing the target nucleic acid to the polymerase comprises exposing the target nucleic acid to the polymerase sequentially or as a mixture. The method further includes removing the functional group that reversibly reduces growth of the target nucleic acid, thereby permitting growth of the target nucleic acid. Exposing the target nucleic acid to the polymerase comprises contacting the target nucleic acid with the polymerase in a microfluidic solution, and the method further comprises repeating determining the mass shift and removing the functional group that reversibly reduces growth of the target nucleic acid, and between the repeating, flushing the microfluidic solution with new material. Exposing the target nucleic acid to the polymerase comprises contacting the target nucleic acid with the polymerase in a microfluidic solution, and the method further comprises repeating determining the mass shift and removing the functional group that reversibly reduces growth of the target nucleic acid, and between the repeating, allowing the microfluidic solution to remain undisturbed.

Particular implementations of the nucleic acids classification by monitoring surface hybridization can provide one or more of the following advantages. Nucleic acids can be identified with high accuracy. The mass can be quantized, pre-formulated and applied in a one-step process; therefore, providing a one-to-one correspondence between binding events and added mass which allows for precise quantification. The system is configured to enable real time detection of binding and unbinding events. The system can be adapted to accurately detect allelic variants by modifying the hybridization conditions in small increments, which can be adjusted to improve the accuracy. The test system can be optimally packed with the maximum number of probes that allows targets to bind to the capture probes. The number of test nucleic acids can be an order of magnitude higher than the number of capture probes. The system can deliver high signal to noise ratio and it can also provide immunity to electrical noise by generating a digital output, which can be processed on the microarray chip or transmitted to an external processor or computer for processing of the latch circuit. The system can be less susceptible to errors from biological, electrical, mechanical or environment changes due to controlled modification of parameters during data capture. The system can identify targets in samples that contain more target nucleic acids than complementary capture nucleic acids, making the system less susceptible to the concentration of targets in a sample. The system can require significantly less time to identify targets. The system can accurately identify targets in the presence of perfectly complementary and nearly perfectly complementary capture nucleic acids. In order to increase the sensitivity or dynamic range of the test system, secondary reagents can be added. The latter reagents can add significant signal by directly adding long sequences of nucleic acids that do not compete for binding to the capture nucleic acids or by incorporating small molecules into the target nucleic acids that can interact with much larger compounds in an independent step.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DETAILED DESCRIPTION

Figure 1:
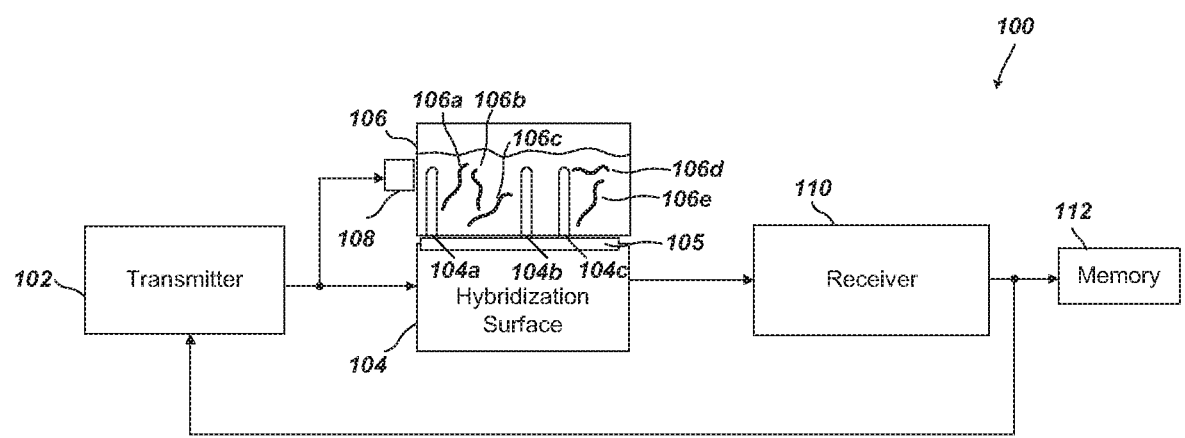
FIG. 1 is a schematic diagram of an example test system configured to classify nucleic acids.

Implementations of the present disclosure are generally directed to classification of test nucleic acids based on monitoring association and dissociation rates. More particularly, implementations of the present disclosure are directed to modifying and monitoring hybridization preference by changing under controlled conditions hybridization selectivity, hybridization specificity and the quantity or relative quantity of test nucleic acids hybridized to capture probes and the (relative) rate or (relative) quantity of association or dissociation. Hybridization can be defined as the base pairing of two single stranded nucleic acids to form a double stranded nucleic acid. The term hybridization can be used interchangeably with binding.

A test nucleic acid can be any compound that contains nucleobases. For example, a test nucleic acid can be a biopolymer that includes nucleobases. Test nucleic acids include deoxyribonucleic acid (DNA), ribonucleic acid (RNA), analogs that contain altered backbones such as peptide nucleic acids (PNA), or nucleobase analogs. A nucleic acid may include functional groups or large compounds that assist their identification, characterization or classification of properties. The functional groups can include fluorophors, chromophors, redox active metals, biotin, or other small molecule. Other test samples include extended single strand or double strand DNA, proteins, peptides, lipids, carbohydrates or hybrids of these compound classes.

The test nucleic acid can be a target nucleic acid or non-target nucleic acid. A target nucleic acid can be a compound of interest that contains nucleobases.

A capture probe can be a compound including nucleobases that can hybridize with a target nucleic acid. A capture probe can be modified at one of the termini in order to enable covalent attachment or non-covalent interaction with a hybridization surface (e.g., solid surface or particulates). For example, functional groups that enable covalent attachment of the capture probes to the solid surface or particulates that are intrinsically reactive or are modified with nucleophilic or electrophilic functional groups include, but are not limited to activated esters (e.g., succinimides and maleimides), thiols, sulfides, disulfides, halides, alcohols, amines, hydrazines, and alcohols. Crosslinking agents such as diimide can also be used for attachment of capture probes to the surface. In addition, capture probes can be modified with compounds that enable indirect, non-covalent binding to the solid surface or particulate. For example, when the solid surface or particulate is modified with streptavidin, the capture probe can be modified with biotin or vice versa. Other modifications, such as spacers, can be added in order to enhance the ability of these compounds to hybridize to test nucleic acids. A capture probe can be manufactured using molecular biological enzymes or via a linear or convergent chemical synthetic processes.

Hybridization preference can include changes that assist in the detection and/or quantification of hybridization. Modifying and monitoring hybridization preference enables the distinction of test nucleic acids that differ by one or a few structural changes. In addition, modifications can be incorporated into nucleic acids using the polymerase chain reaction (PCR) or related techniques with the objective of adding significant weight to hybrids formed between test nucleic acids and capture probes. For example, biotin can be incorporated into test nucleic acids with the intent of adding biotin binding proteins such as streptavidin, neutravidin, captavidin or related proteins. Some of these proteins have multiple binding sites that can bind to other biotin-modified compounds that add significant weight to the hybrid. The latter compounds can include but are not limited to biotin-conjugated antibodies, or high molecular weight beads.

In some implementations, the target nucleic acid can be extended significantly outside of the sequence that is recognized by the capture probes in order to add a known mass to the target. The mass can be, but need not be, a significant mass. The method is applicable to long test nucleic acids. The method can enable the differentiation of closely related proteins or other macromolecules. Detection and quantitation of nucleic acid hybridization preference can be performed based on the change in signal characteristics, such as frequency, amplitude, and/or quality factor during the addition or removal of these compounds of known mass, which in some cases can be high molecular weight compounds.

For example, resonators can be used as a mass sensor and the quality factor of a resonator can be degraded by adding various substances to the surface of a resonator. Degrading the quality factor reduces the ability to measure small changes in resonant frequency and therefore reduces the limit of detection of the device. The design of the resonator and the materials on the surface of the resonator can be particularly selected to maintain a maximum possible quality factor. The addition of mass to the target nucleic acid can degrade the quality factor and the change in quality factor can be used to indicate binding and potentially quantitation of binding of the target nucleic acid to capture probes on the surface of a resonator. Changes in quality factor can be correlated to indicate association and/or dissociation of target nucleic acid on the capture probes. Other aspects of the signal characteristics can be alternately or additionally used to detect or quantitate hybridization between a capture probe and a target nucleic acid with added mass.

The target nucleic acid with added mass can be dissociated from a capture probe through additional techniques. For example, specific environmental factors can be used to generate differential stability of nucleic acid hybrids, such that washing can remove the hybrids that are less stable. As another example, if the additional mass has a positive or negative charge, such as nucleic acid, a complementary charge can be used to reduce stability of nucleic acid hybrids. Since the mismatched hybrids are less stable, they can be removed more easily than the matched hybrids.

Using micromechanical devices that detect nucleic acid hybridization due to a frequency shift can be challenging. For example, using gold nano-particles plated by electrochemical deposition of silver to achieve additional mass can be a multi-step process with some possible deficiencies. The plating of silver can increase the potential for galvanic corrosion of the micromechanical device if it is plated on a dissimilar metal or semi-metal. The plating of silver, in some cases, is not fully selective on the gold nano-particles. Silver may precipitate directly from solution and bind to the mass sensor independently of the mass reporter probes causing erroneous detection. In some cases, this requires regular washing of the chamber in order to avoid the accumulation of silver particulates. Washing can aid in discriminating between hybrids of differing stability. Given the stability of the secondary interactions, for example biotin and streptavidin, washing can provide sufficient energy to cause less stable hybrids to dissociate while leaving more tightly associated hybrids associated on the sensor surface. After weakly hybridized nucleic acids are removed, the hybridization conditions can be modified to be less stringent. This permits dissociation and recovery of tightly bound nucleic acids.

Quantification can be difficult when using gold nano-particles plated with silver. Since the resulting mass is principally the mass of the plated silver, the uncertainty in the plating rate of the silver creates uncertainty in the detection signal. Using gold nano-particles plated with silver is typically only useful for detecting binding events, not dissociation events. The silver plated onto the probes may exceed the dimensions of the nucleic acid being detected. This could result in encapsulation of the nucleic acid which would inhibit further dissociation events.

In some implementations, the mass can be quantized, pre-formulated and applied in a one-step process. The system provides a one-to-one correspondence between binding events and mass addition, which enables precise quantification. The pre-formulation enables real time detection of binding and unbinding events. The mass beads can be fully soluble when not specifically bound and therefore non-specific binding can be minimized. The method is configured to enable continuous processing including repeated dissociation and re-hybridizing of the nucleic acid after the mass reporters are attached.

Sequencing by synthesis is a specialized form of hybridization in which the shorter strand of a partial hybrid formed between a test nucleic acid and a capture probe can sequentially add an additional modified nucleobase or modified single stranded oligonucleotides, containing at least two nucleotides through the action of DNA polymerases or ligases. At each step, the catalyst forms a phosphodiester bond joining the shorter strand to the nucleobase or oligonucleotide that complements to the template strand. Each input nucleobase or oligonucleotide is modified such that it has a unique molecular weight. The identity of the nucleobase or oligonucleotide is readily determined by measuring the amount of added weight at individual steps. The added mass can be attached to the nucleobase at a position that is not directly involved in base pairing to the base pair complement. In some implementations the added mass may need to be removed after the identity of the nucleobase is determined. In some implementations, the mass is irreversibly attached to the growing DNA strand. In either case, a removable functional group that stops the polymerase from adding more than one nucleotide per sequencing cycle is introduced. This is known as reversible termination. The identity of the nucleobase is made and the reversible terminator is removed.

In some implementations, the test system is configured to perform sequencing analysis on a target nucleic acid. The target nucleic acid can be attached to a surface of a resonator system. The target nucleic acid can be exposed to a polymerase that includes a target nucleotide targeted to a target nucleobase on the target nucleic acid. A mass shift can be determined of the target nucleic acid resulting from the exposure of the target nucleic acid to the polymerase. Based on the mass shift, a characteristic of the target nucleic acid regarding the target nucleobase can be determined. Determining the characteristic can include determining a position of the target nucleobase in the target nucleic acid or a number of positions occupied by the target nucleobase in the target nucleic acid Example Circuit for Classification of Nucleic Acids FIG. 1 illustrates an example test system 100, which can monitor a hybridization process and classify nucleic acids. In some implementations, the example test system 100 can include a transmitter 102, a hybridization surface 104, a hybridization detector 105, a sample 106, a conditioning system 108, a receiver 110 and a memory 112. The hybridization detector 105 can be loaded with capture probes 104a, 104b and 104c. The sample 106 can include test nucleic acids 106a, 106b, 106c, 106d and 106e. One or more test nucleic acids (e.g., 106a, 106b and 106c) can bind to the capture probes 104a, 104b and 104c.

The transmitter 102 can be any type of device capable to excite the detector 105, attached to the hybridization surface 104 and/or provide a control signal to the conditioning system 108. In some implementations, the transmitter 102 includes a programmable microprocessor, capable to autonomously generate and transmit a sequence of signals. In some implementations, the transmitter 102 is connected to a computing device on which the signal sequence is selected. For example, the input of a user interacting with a graphical user interface of the computing device, can select the signal sequence to be generated by the transmitter 102.

The hybridization detector 105 can be any substrate (e.g., hybridization chip) that can be loaded with capture probes 104a, 104b and 104c to enable hybridization. In some implementations, the hybridization detector 105 can be a hybridization microarray. The hybridization microarray can include one or more hybridization detectors 105. In some implementations, the hybridization detectors 105 are mass sensing oscillating resonators. A group of capture probes can be distributed on each of the hybridization detectors 105. In some implementations, the capture probes 104a, 104b and 104c loaded on the hybridization detector 105 can perfectly match or they can be closely related to the target nucleic acids of interest (e.g., one or more of the test nucleic acids 106a, 106b and 106c). The capture probes 104a, 104b and 104c can perfectly match target nucleic acids 106a, 106b and 106c can be aligned to form base pairs of maximum stability. In the case of DNA, this means that guanine (G) base pairs with cytosine (C), and adenine (A) base pairs with thymine (T). The absence of a perfectly matched capture probe can lead to excess hybridization to the best-matched capture probe.

Test nucleic acids 106a-106e in solution can be exposed to capture probes 104a, 104b and 104c using conditions that favor hybridization of the most closely matched sequences, and discourage hybridization of less closely matched sequences. In some implementations, exposing the capture probes 104a, 104b and 104c to the nucleic acids 106a-106e includes contacting the capture probes 104a, 104b and 104c with a solution containing the test nucleic acids, e.g., by submerging the capture probes into the solution.

In some implementations, the hybridization detector 105 can be configured as a two port system as shown in FIG. 1. The hybridization detector 105 attached to the hybridization surface 104 can receive as input a signal generated by the transmitter 102. The transmitter 102 can generate a signal or a set of signals with a known frequency, amplitude and phase. In some implementations, the signal generated by the transmitter 102 is a resonating excitation input. For example, the frequency of the signal generated by the transmitter 102 can be swept over time from a frequency known to be lower than the lowest possible resonant frequency of an oscillating resonator array to a frequency known to be higher than the highest resonant frequency of an oscillating resonator array. The hybridization detector 105 can generate a signal with unknown frequency and phase, the signal characteristics being dependent on the binding of the test nucleic acids 106a, 106b and 106c to the capture probes 104a, 104b and 104c. In some implementations, an alternate detection method can be used to detect the binding of the test nucleic acids 106a, 106b and 106c to the capture probes 104a, 104b and 104c. Examples of alternate detection methods can include fluorescence, electrochemolumenescence, flow cytometry, mass spectrometry or other optical methods compatible with the system 100. Some types of detectors (e.g., flow cytometry and mass spectrometry) can require additional elements to enable integration in the system 100.

The conditioning system 108 can receive as input a signal generated by the transmitter 102, which controls the actuation of one or more conditioning parameters. The conditioning system 108 can be located in the proximity of the sample 106, enabling the modification of the hybridization process between the test nucleic acids 106a, 106b and 106c and the capture probes 104a, 104b and 104c. For example, the conditioning system 108 can modify the intramolecular and/or intermolecular base pairing. The conditioning system 108 can gradually modify the hybridization conditions, while the output signal of the hybridization detector 105 attached to the hybridization surface 104 is monitored. Monitoring the output signal of the hybridization detector 105 attached to the hybridization surface 104 enables the identification of the hybridization conditions at which a particular number of capture probes 104a, 104b and 104c formed duplexed nucleic acid with the test nucleic acids 106a, 106b and 106c. In some implementations, the accuracy of the classification of the test nucleic acids 106a, 106b and 106c can be improved by decreasing the increments with which the conditioning parameters are changed.

The conditioning system 108 can include one or more units and generate one or more conditioning parameters. Conditioning parameters can include temperature, charge, motion, and buffer chemistry. For example, increasing temperature and negative charge increase hybridization stringency.

In some implementations, the conditioning system 108 can be a heater and/or cooler that can regulate the temperature at which the hybridization takes place. For example, temperature can be changed in a linear or in a nonlinear or a discrete manner to maximize excess binding of the test nucleic acid (e.g., one of test nucleic acids 106a-106e) to the most correctly matched capture probe (e.g., one of capture probes 104a, 104b and 104c). The location of the capture probes at different temperatures, associated with the nucleic acid hybrid can be used to determine the identity of the test nucleic acid. In some implementations, the conditioning system 108 can include a set of electrodes that can modify the electric field in which the hybridization takes place.

In some implementations, the conditioning system 108 can be a chemical conditioning system that can add chemical compounds to modify the composition, the concentration and/or the pH of the environment in which the hybridization takes place. Examples of chemical additives used to change hybridization can include, but are not limited to, sodium chloride, sodium perchlorate, magnesium chloride, and dibasic sodium phosphate. Other examples of chemical additives that can be used to change hybridization are: metal chelating agents such as ethylenediamine N-, N-,N'-,N'-tetraacetic acid (EDTA) and related compounds. Other examples of chemical additives that can be used to change hybridization include organic reagents that differ in their impact on base pairing stability. Examples of organic reagents that can modify hybridization include but are not limited to N,N'-dimethyl formamide (DMF), dimethylsulfoxide (DMSO), and alcohols including ethanol, methanol, isopropanol, and n-propanol. Organic substances that may bind or otherwise alter hybridization behavior of double stranded nucleic acids include acetic acid, propionic acid, malic acid, guanidine hydrochloride, SBYR green and Coumassie Blue, or detergents such as sodium dodecyl sulfate, polysorbate 20, polysorbate 80, or sodium docusate. Chaotropes, such as urea and guanidine hydrochloride can also be used to change hybridization behavior.

In some implementations, the conditioning system 108 can set a preconditioning phase. The preconditioning phase can be used at the start of each experiment to minimize base pairing between the nucleic acids 106a-106e and the capture probes 104a, 104b and 104c. The hybridization conditions can be changed to lower stringency to enable the formation of the most stable hybrids.

The receiver 110 receives and processes the signals generated by the hybridization detector 105. The receiver 110 can be any type of device capable to read and process the output signal generated by the hybridization detector 105 attached to the hybridization surface 104. Within the context example of the hybridization detector 105 attached to the hybridization surface 104 including resonator arrays, the receiver 110 can be a phase detector. In some implementations, the transmitter 102 and the receiver 110 can form a single unit, which can both transmit and receive signals. In some implementations, the transmitter 102 and the receiver 110 can form two separate units and the output signal of the receiver 110 is sent to the transmitter 102, enabling the termination or modification of the signal sequence based on particular conditions.

In some implementations, hybridization can be monitored with the receiver 110 during incubation in order to provide feedback information. The feedback information can be used by the transmitter 102 to guide changes in conditioning system 108. The changes performed by the conditioning system 108 can enable preferential formation of complementary hybrids. Once the test system 100 classifies a target nucleic acid, the transmitter 102 can halt the signal sequence, enabling the conditioning system 108 to maintain a particular set of conditioning parameters.

The memory 112 receives data from the receiver 110 and stores information within the test system 100. In some implementations, the memory 112 can continuously receive data from the receiver 110 to store information about the entire hybridization monitoring procedure. In some implementations, the memory 112 receives data from the receiver 110 at particular steps of the hybridization monitoring procedure (e.g., upon the classification of a target nucleic acid or at critical changes in conditioning parameters). The data stored by the memory 112 can be transferred over a network to a computing system.

The memory 112 can be a computer-readable medium. In some implementations, the memory 112 is a volatile memory unit. In another implementation, the memory 112 is a non-volatile memory unit. For example, the memory 112 can be a floppy disk device, a hard disk device, an optical disk device, or a tape device.

One or more components of the test system 100 described with reference to FIG. 1, can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor can receive instructions and data from a read-only memory or a random access memory or both. The essential elements of a computer are a processor for executing instructions and one or more memories for storing instructions and data. The computer can also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features of test system 100 can be implemented on a computer having a display device such as an LCD (liquid crystal display) monitor for displaying information to the user and a keyboard and a pointing device such as a mouse, a trackball or a touch screen by which the user can provide input to the computer.

The features of test system 100 can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The test system 100 can include clients and servers. A client and server are generally remote from each other and typically interact through a network, such as the described one. The relationship of client and server arises by virtue of computer programs running on the respective computers and having a client-server relationship to each other. In some implementations, a client can access test system 100 to initiate the hybridization process and access the results of the nucleic acids classification on a computer system.

Example Classification of Test Nucleic Acids by Hybridization to Capture Probes

Figure 2A:
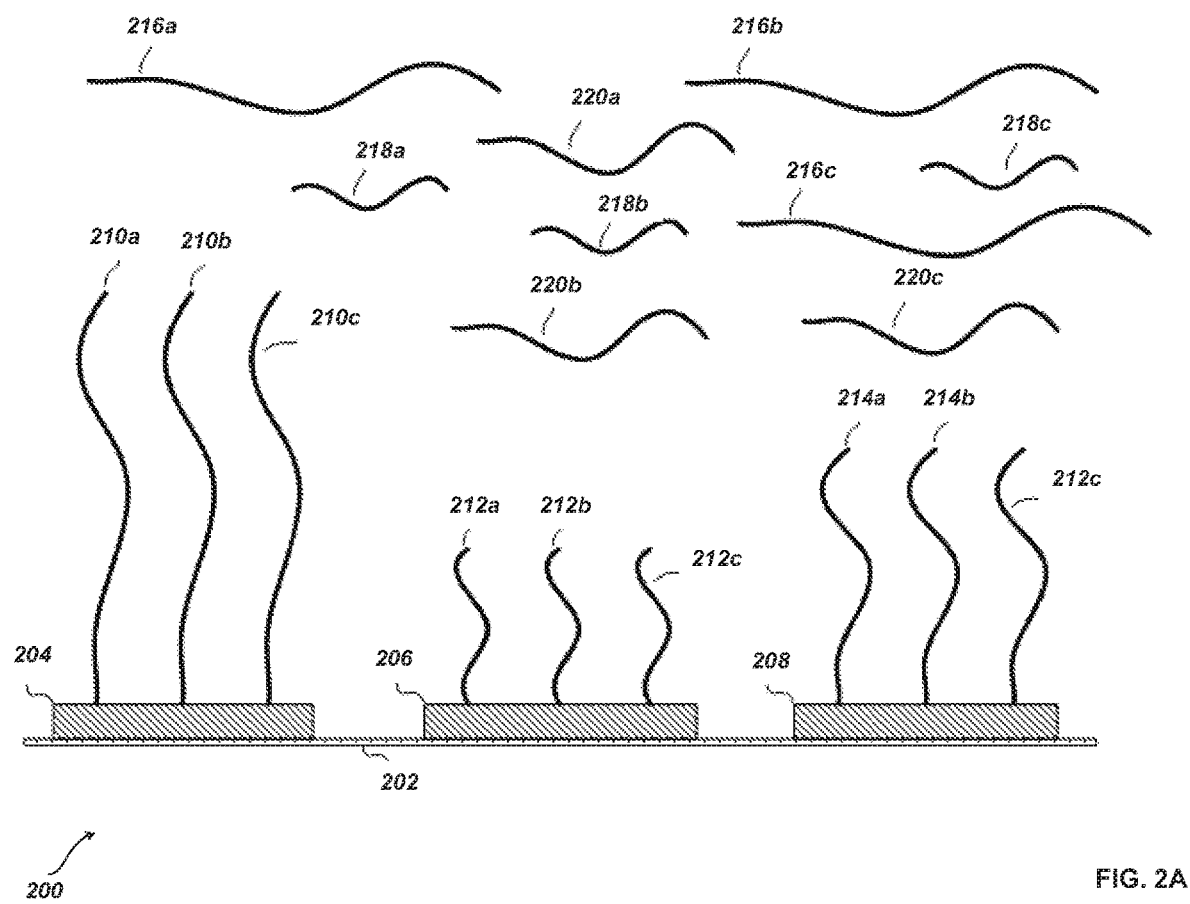
FIG. 2A is schematic diagram of example single-stranded nucleic acid capture probes on surfaces in the presence of unassociated single-strand test nucleic acids in solution.

FIGS. 2A and B are schematic diagrams of example systems 200 used for classification of test nucleic acids by hybridization to capture probes. The system 200 includes a support 202 including one or more attachment surfaces 204, 206 and 208. The support 202 can be included in the hybridization surface 104, described with reference to FIG. 1. The attachment surfaces 204, 206 and 208 enable the attachment of capture probes 210a, 210b, 210c, 212a, 212b, 212c, 214a, 214b, and 214c, which can bind with the test nucleic acids 216a, 216b, 216c, 218a, 218b, 218c, 220a, 220b, and 220c. In some implementations, the number of test nucleic acids can be an order of magnitude higher than the number of capture probes. The test nucleic acids can be grouped based on the sequence type (e.g., group 1 of test nucleic acids including nucleic acids 216a, 216b and 216c, group 2 of test nucleic acids including nucleic acids 218a, 218b and 218c and group 3 of test nucleic acids including nucleic acids 220a, 220b and 220c). Capture probes with nucleic acid sequences complementary or substantially complementary to the target nucleic acids can be attached to a surface and the test nucleic acids can be mixed with the capture probes using conditions that encourage hybridization. For example, each of the attachment surfaces 204, 206 and 208 can be loaded with a particular type of capture probes. Each of the attachment surfaces 204, 206 and 208 can be loaded with capture probes of particular length and sequence. Within the context example, the attachment surface 204 can be loaded with single-stranded nucleic acid capture probes 210a, 210b and 210c, the attachment surface 206 can be loaded with single-stranded nucleic acid capture probes 212a, 212b and 212c, and the attachment surface 208 can be loaded with single-stranded nucleic acid capture probes 214a, 214b, and 214c.

Figure 2B:
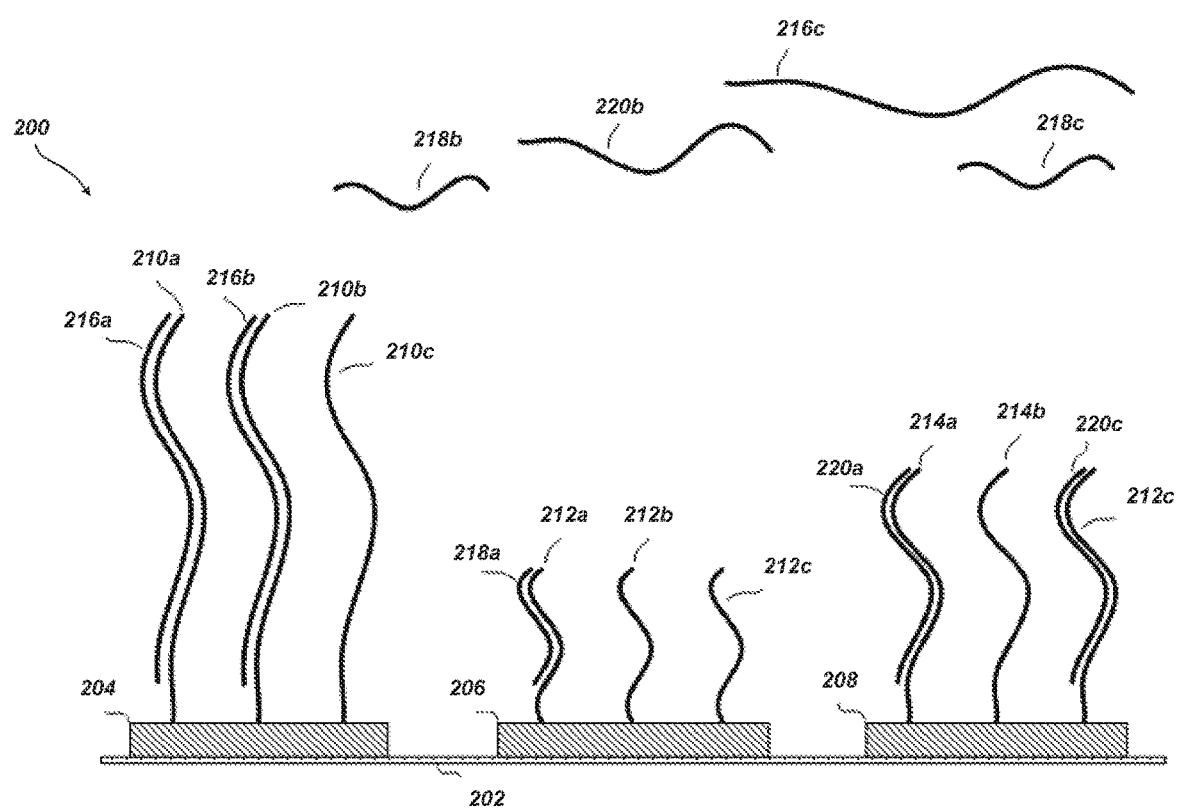
FIG. 2B is a schematic diagram of example formed nucleic acid hybrids on surfaces.

As illustrated in FIG. 2A the single-stranded nucleic acid capture probes 210a, 210b, 210c, 212a, 212b, 212c, 214a, 214b, and 214c can be preconditioned, as described with reference to FIG. 1, to be in the presence of unassociated single-strand test nucleic acids 216a, 216b, 216c, 218a, 218b, 218c, 220a, 220b, and 220c. As illustrated in FIG. 2B, the modification of the conditioning parameters enables the hybridization of some of the single-stranded nucleic acid capture probes (e.g., 210a, 210b, 212a, 214a, and 214c) with some of the single-strand test nucleic acids (e.g., 216a, 216b, 218a, 220a, and 220c).

The test nucleic acid can be classified as being one or more target nucleic acids by identifying the surface associated with the capture probe that hybridizes to the test nucleic acid. The conditioning parameters can be modified, as described with reference to FIG. 1, to enable the formation of well- or perfectly-matched hybrids (e.g., double-stranded hybrid including capture probe 210a with test nucleic acid 216a).

In some examples, the test nucleic acids (e.g., 216a, 216b, 218a, 220a, and 220c) can be hybridized by capture probes and reporter compounds to form a trimeric hybrid. The sequences of capture and reporter probes can include sequences that can hybridize to the same region of the test nucleic acid and the hybridization competition can lead to strand displacement of the reporter compounds. The length of the nucleic acids and the similarities in sequences between the coexistent types of nucleic acids can influence the number of modification of conditioning parameters required to enable the formation of well- or perfectly-matched hybrids and the classification of the test nucleic acids.

Example Classification of Closely Related Test Nucleic Acids

Figure 3A:
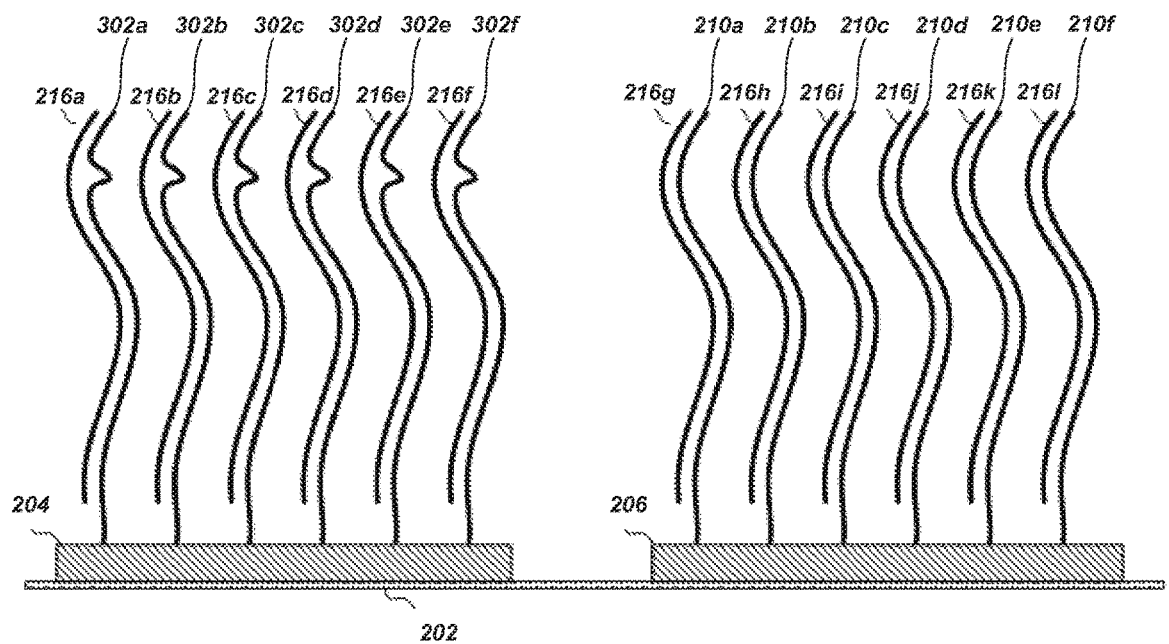
FIG. 3A is a schematic diagram of example mismatched hybrids relative to perfectly-matched hybrids.

FIGS. 3A and B are schematic diagrams of an example system 300 that can be used for the classification of closely related nucleic acids. The system 300 includes a support 202 including one or more attachment surfaces 204 and 206. The support 202 can be included in the hybridization surface 104, described with reference to FIG. 1. The capture probes 302a-302f and 210a-210f are loaded on the attachment surfaces 204 and 206, respectively and can bind with the test nucleic acids 216a-216f.

Capture probes 302a-302f have the same sequence and are bound to attachment surface 204. Capture probes 216a-216f have the same sequence and are bound to attachment surface 206. The sequences of capture probes 302a-302f and 210a-210f are long and closely related. As illustrated in FIG. 3A, test probes 216a-216l have the same sequence but hybridize differently to capture probes 302a-302f than to capture probes 210a-210f due to the small differences in the capture probe sequences. The kinks in the capture probes 302a-302f are the result of mismatched hybridization.

In some implementations, mis-matched hybridization can be avoided or minimized by exposing the target nucleic acids 216a-216l to capture probes 302a-302f and 210a-210f using conditions that favor hybridization of complementary matched sequences, and discourage hybridization of non-complementary matched sequences. For long and closely related alleles, the classification of conditioning parameters that enable perfect matching criteria could require multiple iterations performed in small increments.

Figure 3B:
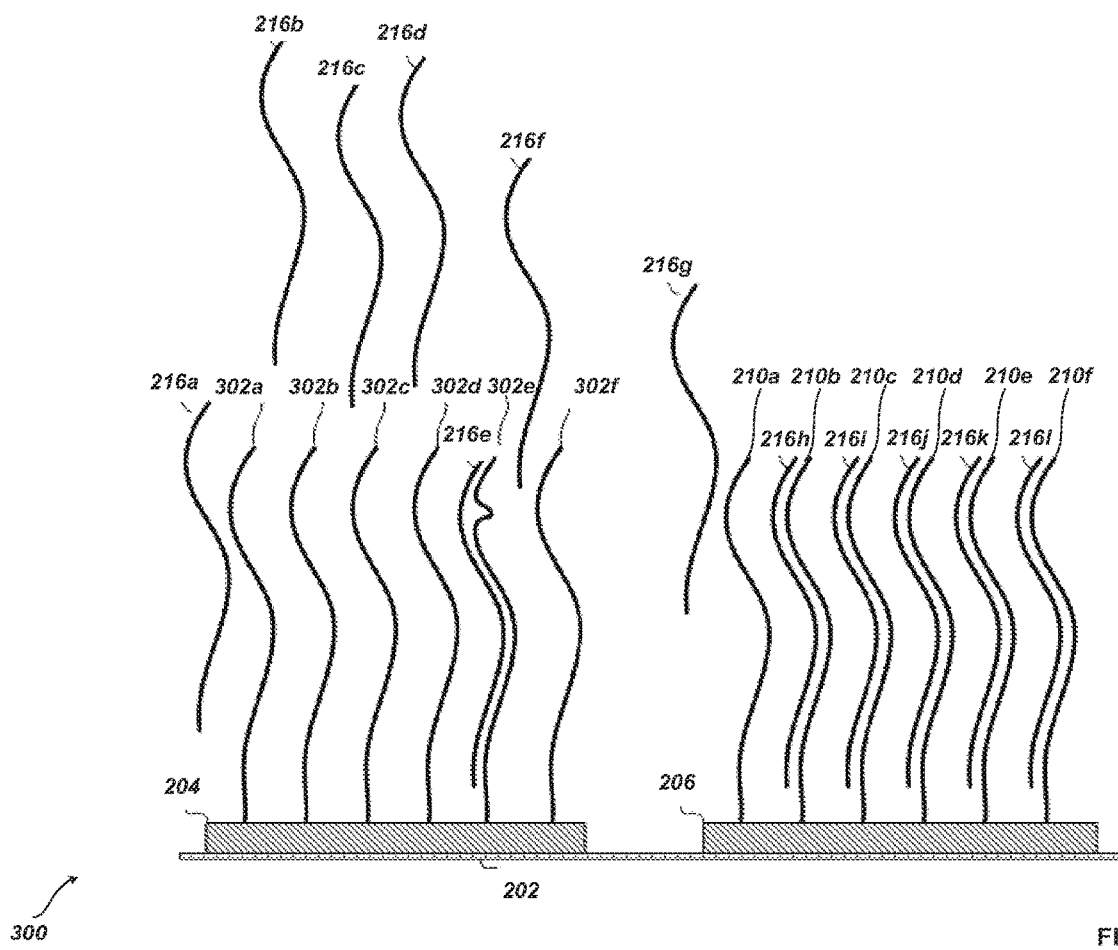
FIG. 3B is a schematic diagram of an example hybridization condition where mismatched hybrids dissociate faster than perfectly-matched hybrids.

In some implementations, the preconditioning of the system 300 is used, as described with reference to FIG. 1, to minimize hybridization between test nucleic acids 216a-216l and capture probes 302a-302f and 210a-210f. Preconditioning can minimize intramolecular or intermolecular base pair formed by the compounds. The conditioning parameters can be slowly changed to lower stringency, to favor hybridization to complementary capture probes 210a-210f, as illustrated in FIG. 3B. As stringency is decreased, test nucleic acids 216a-216l can hybridize to capture probes 210a-210f.

In some implementations, the hybridization conditions and rates between test nucleic acids 216a-216l and capture probes 210a-210f can be determined through modeling and/or empirical methods. By monitoring the rate of association, quantity and location of hybridization, it is possible to determine the identity of test nucleic acids. In some implementations, conditioning parameters are selected to favor hybridization between test nucleic acids 216a-216l and complementary capture probes 210a-210f as well as mismatched capture probes 302a-302f as shown in FIG. 3 and described above.

Example System for Hybridization Optimization

Figure 4A:
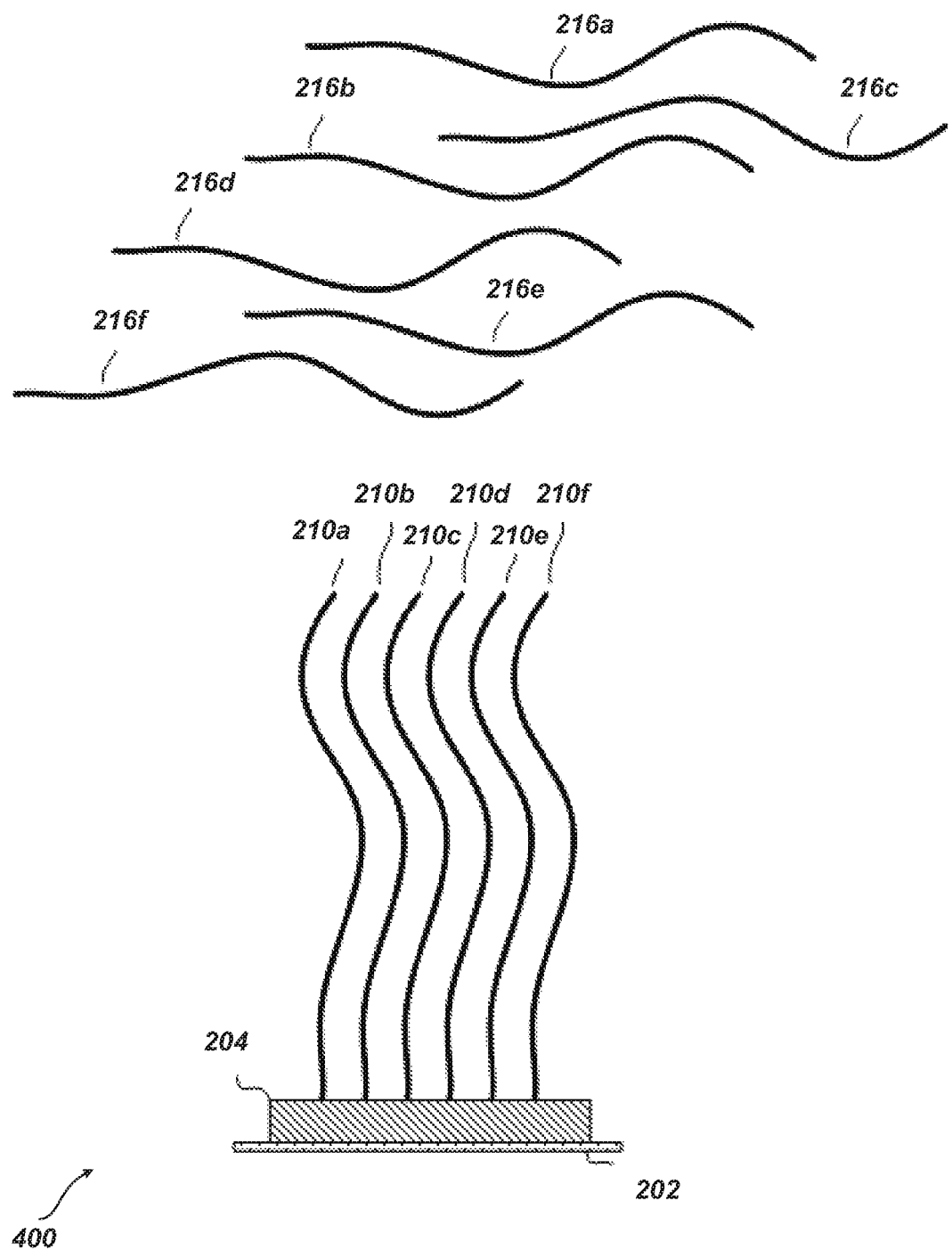
FIG. 4A is a schematic diagram of example dense packing of capture probes in the presence of test nucleic acids.
Figure 4B:
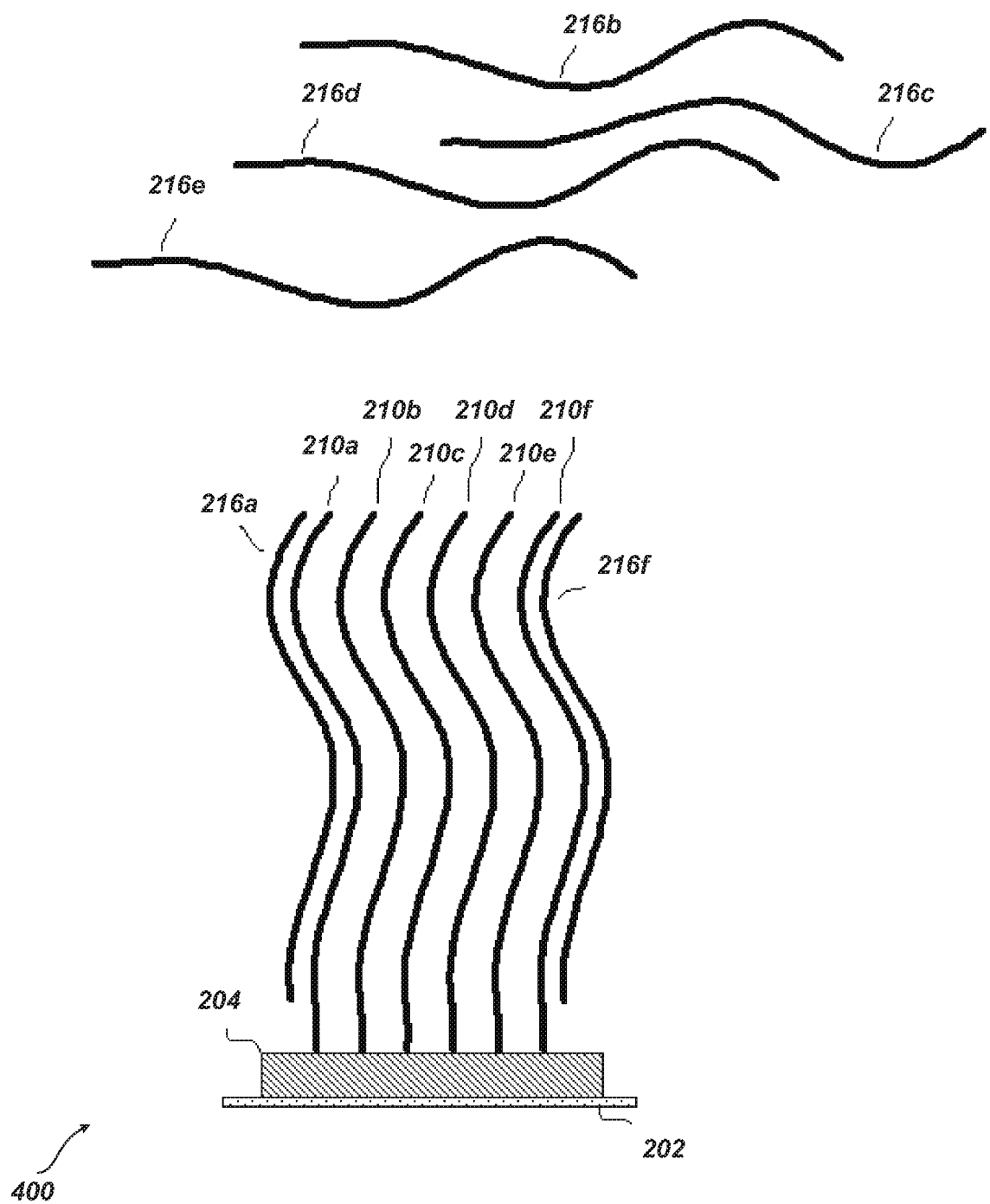
FIG. 4B is a schematic diagram of example dense packing of capture probes that inhibits permeation of test nucleic acids and limits hybridization.

FIGS. 4A and B are schematic diagrams of an example system 400 that can be used for the optimization of capture probe density. The system 400 includes a support 202 including an attachment surface 204. The support 202 can be included in the hybridization surface 104, described with reference to FIG. 1. The capture probes 210a-210f are loaded on the attachment surface 204 and can bind with the test nucleic acids 216a-216f.

In some implementations, the density of capture probes 210a-210f can be used to enhance hybridization preference. For example, hybridization can be optimized by considering the hydrodynamic radius ($R_H$). Mis-matched hybrids form kinks, hairpin loops, chain bending and other elements of secondary structure that increase $R_H$. High density of capture probes 210a-210f are tightly packed on the attachment surface 204 can repel test nucleic acids 216a-216f from permeating the bed of capture probes 210a-210f, rendering the differences in $R_H$ unimportant. For example, the density of capture probes 210a-210f on the attachment surface 204 can range between $10^8$ to $10^{14}$ capture probes per cm$^2$.

As illustrated in FIGS. 4A and B, the capture probes 210a-210f bound to attachment surface 204 have the same sequence and are complementary to test nucleic acids 216a-216f. Because of the high density of the capture probes 210a-210f, the distance between neighboring strands is too close to permit penetration of a significant number of test strands. In the example illustrated by FIG. 2B, steric crowding occurs with little or no hybridization. The outlier capture probes 210a and 210f, which are located at the outside edge of attachment surface 204 are accessible and hybridize with test nucleic acids 216a and 216f, respectively. Test nucleic acids 216b-216e remain dissociated in the medium, unable to penetrate into the capture probe matrix.

Example System for Hybridization Optimization

Figure 5A:
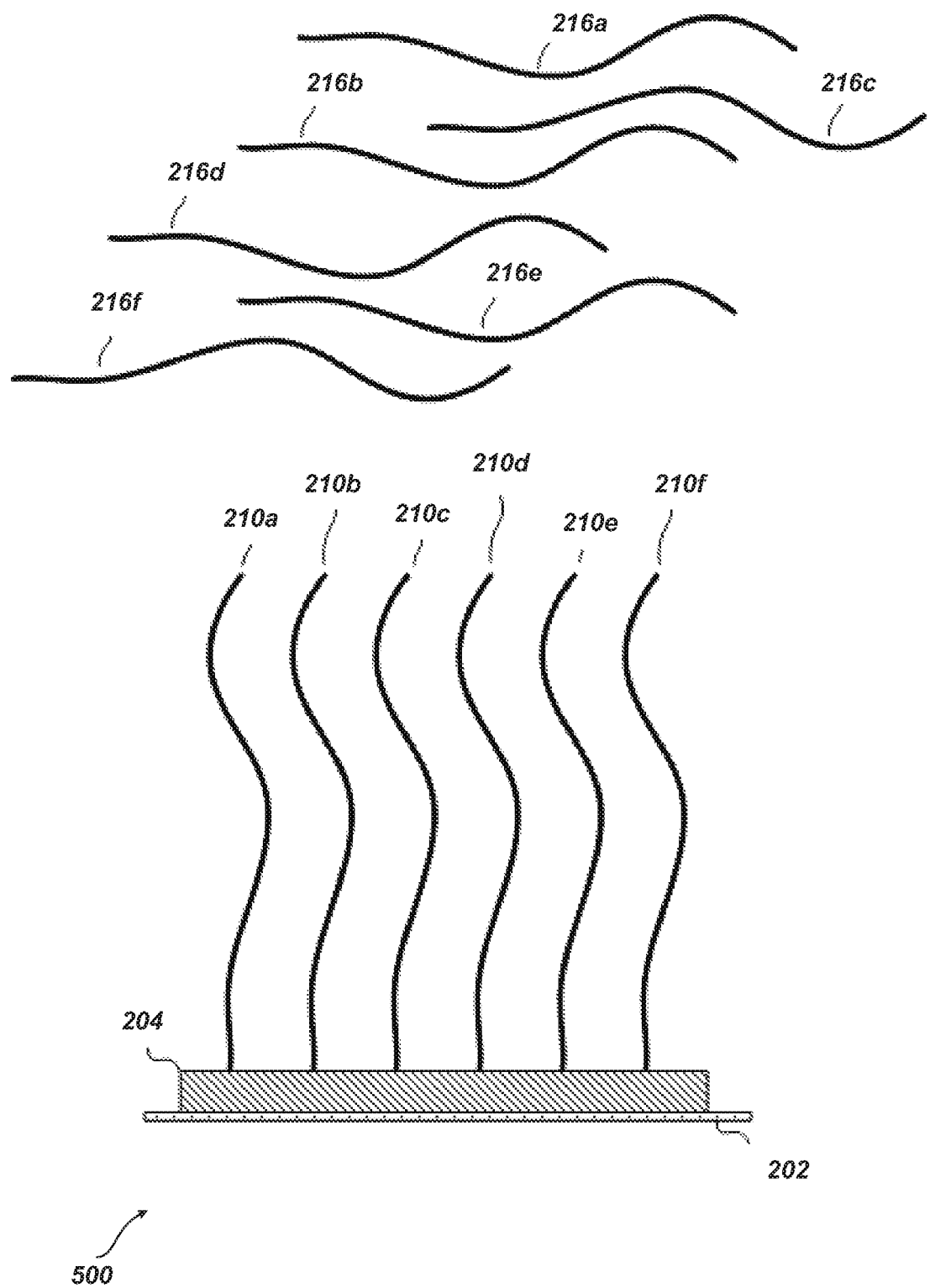
FIG. 5A is a schematic diagram of example capture probes at lower density in the presence of test nucleic acids.

FIGS. 5A and B are schematic diagrams of an example system 500 that can be used for the optimization of capture probe density. The system 500 includes a support 202 including an attachment surface 204. The support 202 can be included in the hybridization surface 104, described with reference to FIG. 1. The capture probes 210a-210f are loaded on the attachment surface 204 and can bind with the target nucleic acids 216a-216f.

Low density of capture probes 210a-210f on the attachment surface 204, readily permit permeation and steric issues are less important. At intermediate density, formation of mis-matched hybrids increases $R_H$ such that the hybrid is close to neighboring capture probes 210a-210f and inhibits additional hybridization due to steric crowding.

Figure 5B:
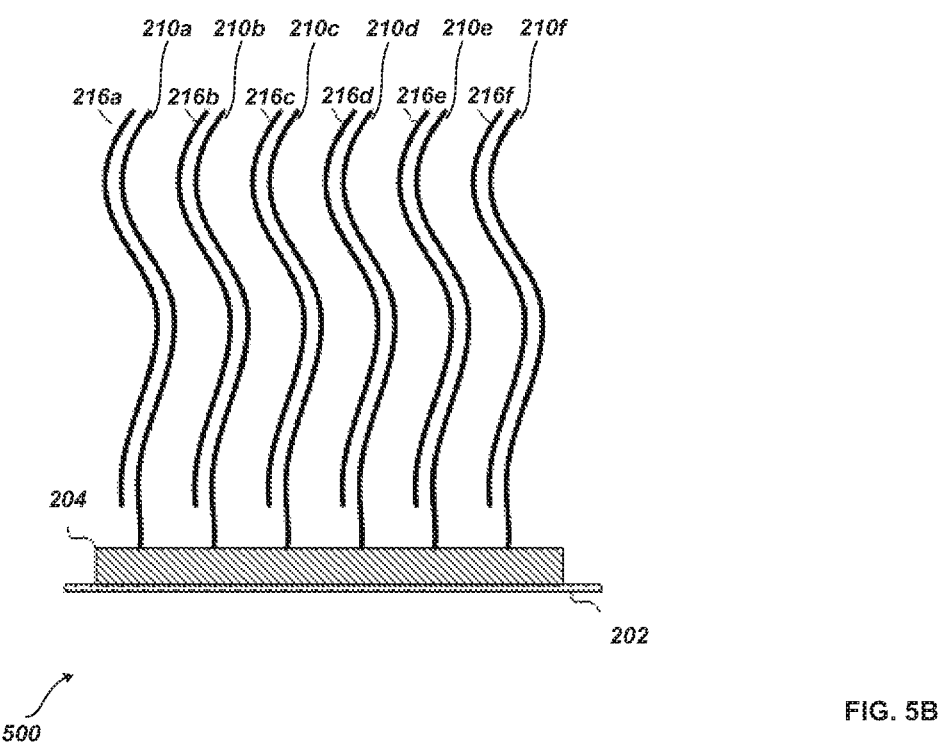
FIG. 5B is a schematic diagram of example capture probes at lower density, that can interact and hybridize with complementary test nucleic acids.

As illustrated in FIGS. 5A and B, the capture probes 210a-210f bound to attachment surface 204 at low density enable perfectly- or closely matched target nucleic acids to permeate the capture probe 210a-210f matrix and form hybrids. In FIG. 5A, capture probes 210a-210f, attached to attachment surface 204, are exposed to complementary test nucleic acids 216a-216f. As shown in FIG. 5B, the spacing permits permeation of the test nucleic acids 216a-216f, enabling hybridization to occur between capture probes 210a-210f and complementary target nucleic acids, 216a-216f.

Example System for Measurement Optimization

Figure 5C:
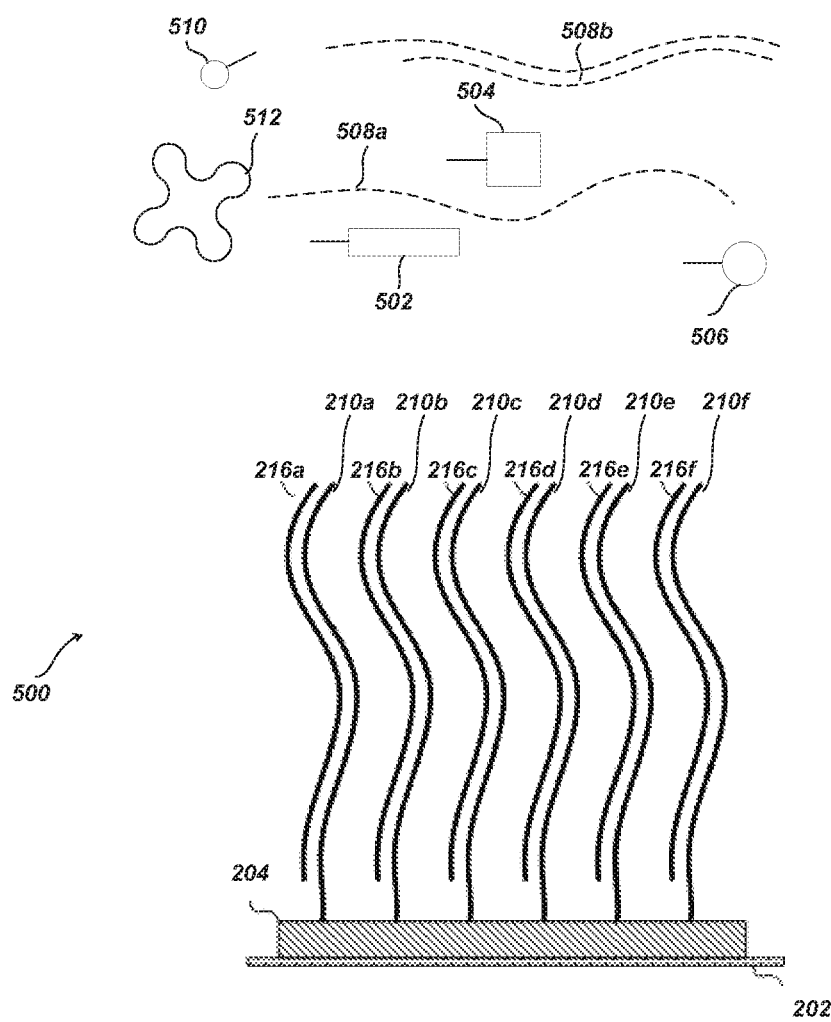
FIG. 5C is a schematic diagram of example capture probes hybridized with complementary test nucleic acids in the presence of unassociated mass reporters in solution.

FIGS. 5C and D are schematic diagrams of an example system 500 including markers that can be used for the optimization of target nucleic acid identification. The system 500 includes a support 202 including an attachment surface 204. The support 202 can be included in the hybridization surface 104, described with reference to FIG. 1. The capture probes 210a-210f are loaded on the attachment surface 204 and bound to the target nucleic acids 216a-216f.

The solution of the system 500 can include one or more types of markers. In the example illustrated in FIGS. 5C and D, the markers are mass reporters 502. In some implementations, the markers can be optical markers (e.g., fluorescent proteins) that can provide a response to an irradiation having a particular wavelength or other types of markers. For attaching the markers (e.g., mass reporters 502) to the target nucleic acids 216a-216f one or more unassociated compounds can be used. Examples of unassociated compounds include reactive moiety 506, functional group 504, single stranded extension of target nucleic acid 508a, double stranded extension of target nucleic acid 508b, high affinity antigen 510 and high affinity macromolecule 512. The reactive moiety 506 and the functional group 504 can include a bridge attachment to target nucleic acid. The reactive moiety 506 can react with the functional group 504 to form a stable covalent bond. Examples of reactive moiety 506 that can react with the functional group 504 can include amines with active esters, sulfhydryl groups, or other compounds that can attach or detach from each other in the presence of particular agents. The mass reporter 502 can be a compound of known mass, a high molecular weight compound, a protein, an antibody, a streptavidin, a polymer or a bead. The high affinity antigen 510 can be a biotin. The high affinity macromolecule 512 can be a streptavidin.

Figure 5D:
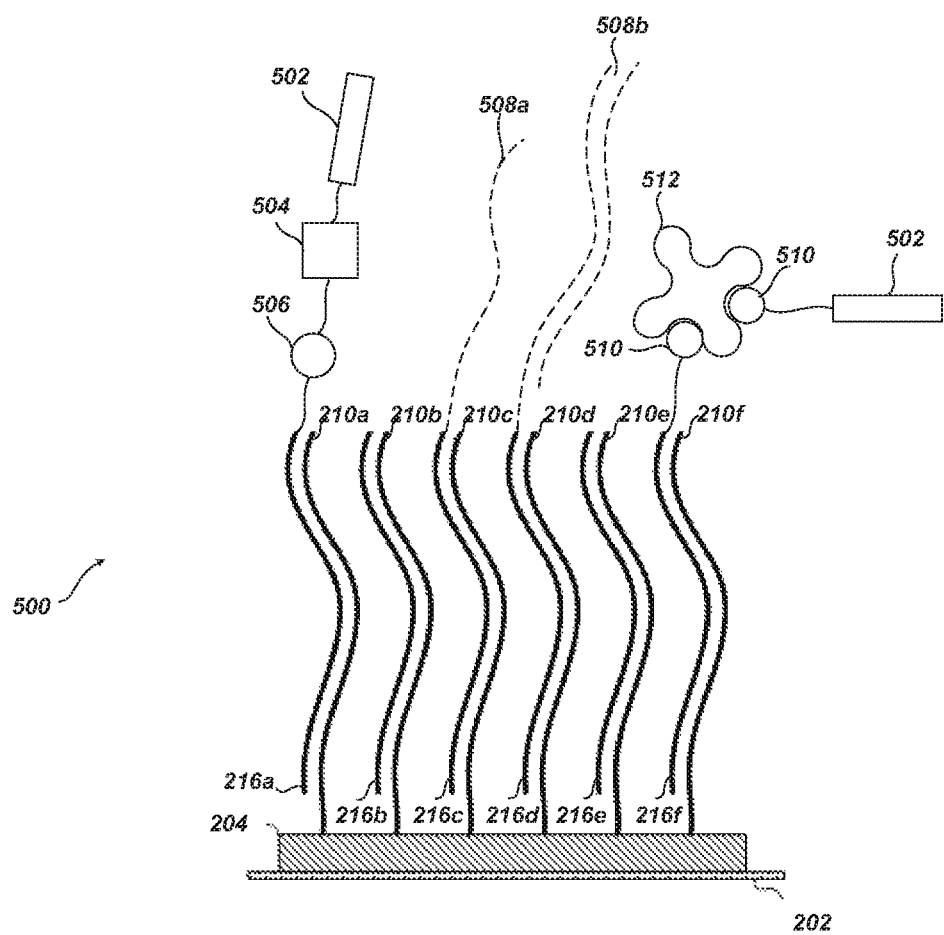
FIG. 5D is a schematic diagram of example capture probes hybridized with extended test nucleic acids.

Some of the target nucleic acids 216a-216f can interact with one or more of the unassociated compounds. As illustrated in FIG. 5D, the bridge of the reactive moiety 506 or of the functional group 504 can attach the group, including the reactive moiety 506 and the functional group 504, to the target nucleic acid 216a. The group, including the reactive moiety 506 and the functional group 504 can bind to the mass reporter 502, thereby increasing the detected mass.

In some implementations, a single stranded nucleic acid 508a or a double stranded extension of target nucleic acid 508b can be added as a tag to a particular target nucleic acid 216c or 216d, respectively. Both the target nucleic acid (216c or 216d) and the distal strand forming the extension nucleic acid 508a and 508b can be amplified to add weight by attaching one or more sets of primers. In some implementations, a region of the target nucleic acid can be selectively targeted to increase the mass of the target nucleic acid without affecting the hybridization with the capture probe.

In some implementations, a group including a high affinity antigens 510 and high affinity macromolecule 512 can be attached to a target nucleic acid 216f. One or more additional high affinity antigens 510 can be further attached to the high affinity macromolecule 512 to add one or more mass reporters 502. Various other extensions can be attached to the target nuceic acids and a plurality of modifications can be made to control the addition of mass to target nucleic acids. For example, even though FIGS. 5C and 5D illustrate different types of possible extensions, in some implementations, the identification of target nucleic acids can be optimized by using a single type of extension, each compound used for the extension, being added to the solution of the system 500 in a controlled manner.

Example Flowchart

Figure 6:
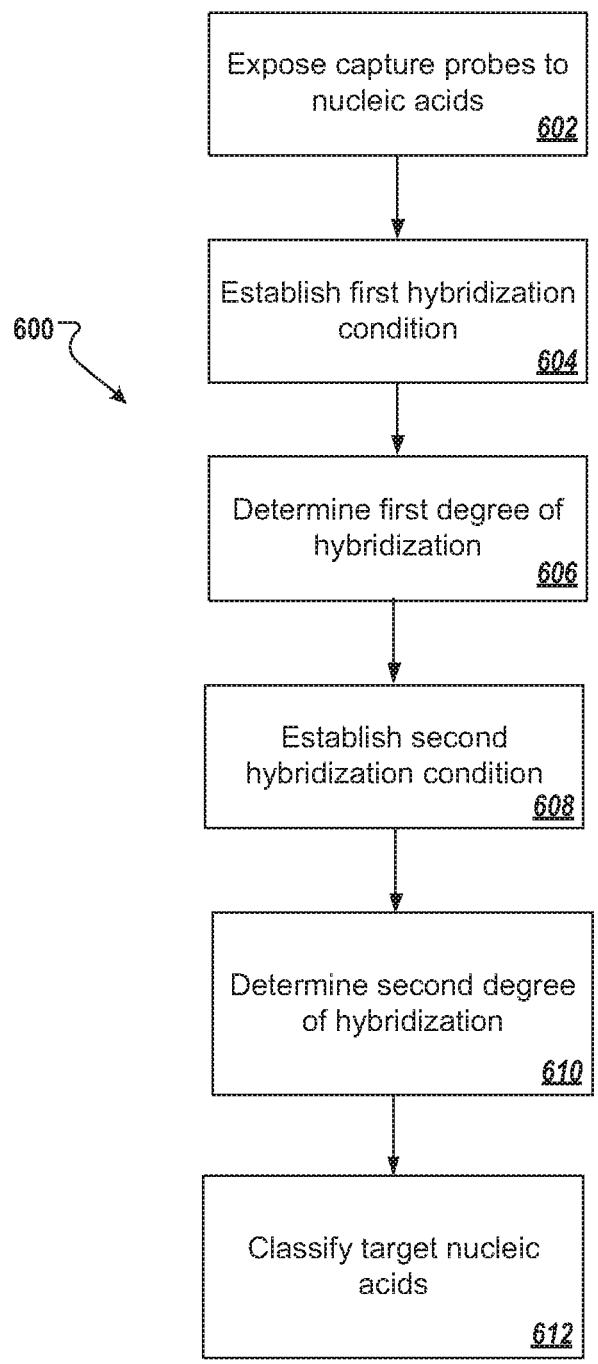
FIG. 6 is a flowchart depicting an example process that can be executed in accordance with implementations of the present disclosure.

FIG. 6 is a flowchart depicting an example process 600 that can be executed in accordance with implementations of the present disclosure. In some examples, the example process 600 can include operations that are performed by a user of the system or by one or more components of the systems described with reference to FIGS. 1-5. The example process 600 is an example test nucleic acids classification protocol with output that can be stored in an internal or external memory. In some implementations, classifying a test nucleic acid includes differentiating a target nucleic acid from a non-target nucleic acid. In case a test nucleic acid is classified as a target, the test nucleic acid can be identified.

One or more capture probes are exposed to test nucleic acids in a test system, the one or more capture probes being attached to a surface 602. The test nucleic acids can include a target nucleic acid that is complementary to a capture probe located at a first location and other target nucleic acids that are complementary to capture probes, attached to other locations on the surface. In some implementations, the test system includes a resonator system configured to measure a mass of an object on at least one surface of the resonator system. The captures probes can be attached to the surface of the resonator system.

A first hybridization condition is established in the test system 604. In some implementations, the first hybridization condition includes setting preconditioning parameters to minimize base pairing between the test nucleic acids and the capture probes. Hybridization conditions can include environmental conditions and components of the solution. Environmental conditions can include temperature, charge, motion, and buffer chemistry. For example, setting a first hybridization condition can include increasing temperature and negative charge.

A first degree of hybridization of the one or more capture probes with the nucleic acid under the first hybridization condition is determined at each location on the surface 606. Determining the first degree of hybridization can include determining the association rate of target nucleic acids to capture probes and/or dissociation rate of target nucleic acids from capture probes at each location. The respective rates of hybridization association or dissociation can be used to determine the relative concentration of each target nucleic acid. The preconditioning parameters can enable the hybridization of particular test nucleic acids with corresponding capture probes at a higher preference than hybridization with other capture probes. For example, increasing temperature and negative charge can increase hybridization stringency between particular capture probes and test nucleic acids.

A second hybridization condition is established in the test system 608. In some implementations, the second hybridization condition is selected to favor hybridization between the target nucleic acid and the one or more capture probes. In some implementations, the hybridization condition can be progressively adjusted (e.g., in small increments) to cover a preset range of values, as described with reference to FIG. 1. After each adjustment, a degree of hybridization of the capture probes with the nucleic acids can be determined at each location on the surface. The hybridization conditions can be continuously or discretely adjusted until the degree of hybridization reaches a threshold degree of hybridization. In some implementations, the hybridization condition can be changed in response to a measurement at one or more locations on the hybridization surface.

A second degree of hybridization of the one or more capture probes with the nucleic acid under the second hybridization condition is determined 610. The second hybridization condition can enable the hybridization of a second set of capture probes. The second set of hybridized capture probes can be different from the first set of hybridized capture probes. In some implementations, determining the first and second degrees of hybridization of the capture probes with the nucleic acid can include measuring the mass on the surface of the resonator system. The second degree of hybridization can be compared to the first degree of hybridization to determine the hybridization condition corresponding to each capture probe. Based on the comparison between the hybridization of different capture probes at different hybridization conditions at multiple locations, the test nucleic acids can be classified 612. The classification of the test nucleic acids as complementary or non-complementary to capture probes, attached to particular locations on the hybridization surface, can enable the identification of test nucleic acids.

In some examples, a test nucleic acid may not have a perfectly complementary capture probe on the test system. In case the perfect match is missing, the identity of the test can be determined by observing the hybridization of target nucleic acids with mis-matched capture probes. In some examples, a test nucleic acid can hybridize to a perfectly complementary capture probe on the test system and a nearly perfectly complementary capture probe on the test system during the hybridization conditions such that the difference in hybridization cannot be used to determine the identity of the test. Utilizing interactive hybridization, the hybridization conditions can be modified multiple times to determine whether a matched or a mis-matched hybridization occurred. Observing mismatched hybridization on multiple capture probes can provide additional information about the identity of the test nucleic acid.

For example, the test system can monitor the melting temperatures of multiple test nucleic acids ($T_X$) at multiple capture probes ($P_X$), as illustrated in Table. 1, to create a signature analysis. Within the context example, the test nucleic acids $T_{29}$ and $T_{30}$ are very closely related. The melting temperature of $T_{29}$ on capture probe $P_{29}$ is 60.2° C. The melting temperature of $T_{30}$ on capture probe $P_{29}$ is 60.0° C. The test system might not have a sufficient resolution to detect the temperature difference between the melting temperatures of the test nucleic acids $T_{29}$ and $T_{30}$ on capture probe $P_{29}$. The melting temperature of the test nucleic acids on different probes can provide additional data to support the classification of the test nucleic acids. Within the context example, the melting temperature of $T_{29}$ on capture probe $P_{28}$ is 59.0° C. The melting temperature of $T_{30}$ on capture probe $P_{28}$ is 58.0° C., being 1° C. lower than the melting temperature of $T_{29}$ on capture probe $P_{28}$. The difference between the melting temperatures of the test nucleic acids $T_{29}$ and $T_{30}$ on $P_{28}$ can be within the resolution of the test system, enabling the differentiation of the test nucleic acids $T_{29}$ from $T_{30}$.

TABLE 1

|  | $P_{28}$ | $P_{29}$ | $P_{30}$ | $P_{31}$ |
| --- | --- | --- | --- | --- |
| $T_{29}$ | 59.0° C. | 60.2° C. | 60.0° C. | 58° C. |
| $T_{30}$ | 58.0° C. | 60.0° C. | 60.2° C. | 59° C. |

In some examples, monitoring the relative amounts of hybridization at distinct locations on the test system over time can be used to provide information that aids in the classification of a test nucleic acid. In one example, the difference in hybridization at two distinct locations at particular times is not easily distinguishable, but hybridization at a later time at a third location can be distinctly different. The time and relative amounts of hybridization at the three locations can be compared against empirical and/or model data to determine the identity of the test nucleic acid. In another example, a perfectly complementary capture probe does not exist for a test nucleic acid on the test system. Within the context example, the timing and amount of hybridization at any location on the test system does not match empirical and/or model data. The time and relative amounts of hybridization at various locations on the test system can be used to determine that a perfectly complementary capture probe does not exist and they can be compared against empirical and/or model data of test nucleic acids with non-complementary capture probes to determine the identity of the test nucleic acid.

The hybridization preference may differ for each allelic hybrid. In some examples, it is possible to determine the relationships between the hybridization parameters and the thermodynamic stability of individual hybrids. In some implementations, a nucleic acid modeling software can be used to calculate the relative stability of hybrids formed between a test nucleic acid and a series of capture probes relative to one or more hybridization parameters.

In some implementations, the impact of hybridization parameters can be determined during the experiment utilizing real-time monitoring. For example, the hybridization parameters can be modified continuously or discretely while hybridization is monitored until a signal indicative of excess hybridization on one of the closely related capture probes is observed.

In some implementations, the process 600 enables concurrent analysis of multiple target nucleic acids is of interest. System parameters can be adjusted to assist simultaneous classification of multiple test nucleic acids based on the analysis of the differences between thermodynamic stability of the hybrid formed between a particular test nucleic acids and a plurality of closely-matched capture probes.

Example Flowchart

Figure 7:
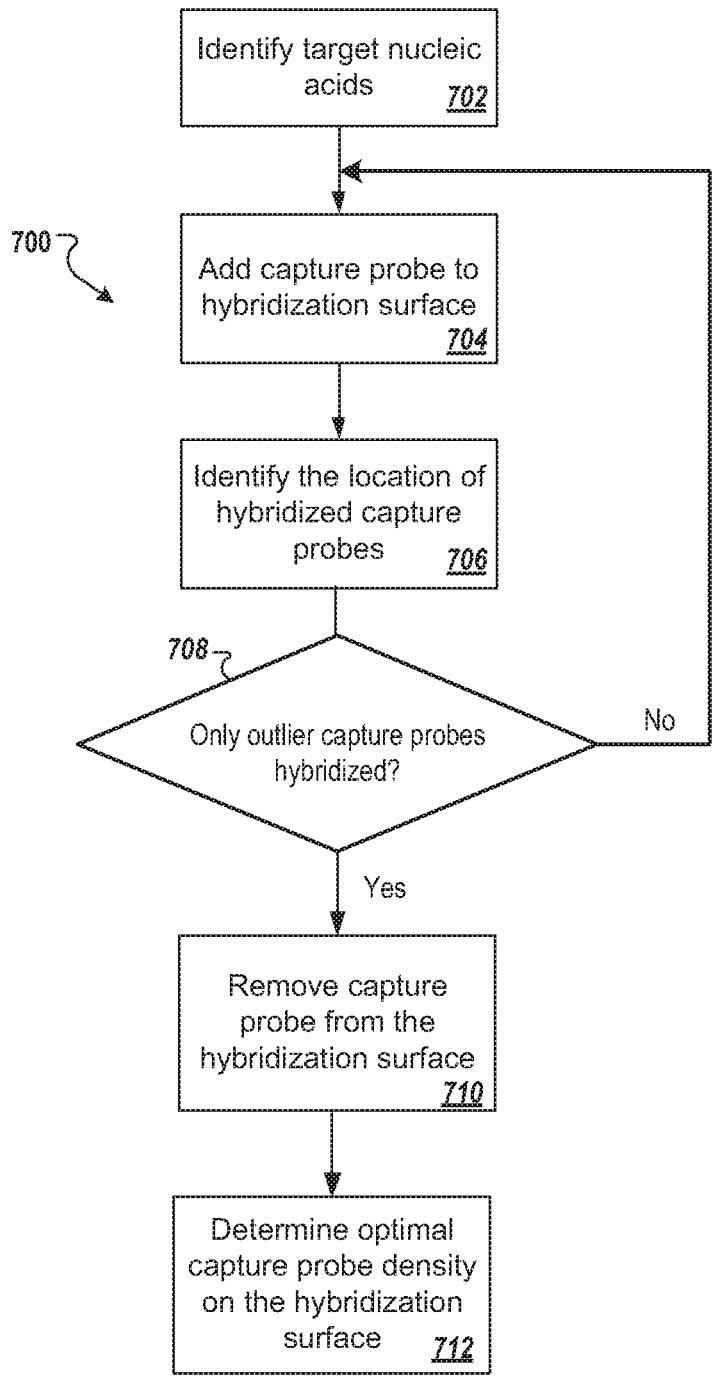
FIG. 7 is a flowchart depicting an example process that can be executed in accordance with implementations of the present disclosure.

FIG. 7 is a flowchart depicting an example process 700 that can be executed in accordance with implementations of the present disclosure. In some examples, the example process 700 can include operations that are performed by a user of the test system or by one or more components of the systems described with reference to FIGS. 1-5. The example process 700 is an example capture probe density optimization protocol with an output that can be stored in an internal or external memory.

Test nucleic acids matching with capture probes can be classified 702. One or more capture probes can be added to the test system to increase the density of the capture probes 704. In some implementations, the capture probes can be randomly added to the test system. In some implementations, the capture probes can be added to the test system in particular locations to maintain the uniform distribution of the capture probes. The modified field of capture probes loaded on the test system is exposed to the test nucleic acids enabling hybridization. In some implementations, hybridization is performed at control hybridization conditions, as described with reference to FIGS. 1, 2 and 6. The location of the hybrids formation is classified. As described with reference to FIG. 4B, if the capture probes are too dense, the target nucleic acids can only hybridize the outlier capture probes.

It is determined whether hybridization is limited to outlier capture probes 708. If hybridization occurred within the capture probe field, additional capture probes are added 704. If hybridization occurred only at outlier capture probes, the system classifies the last selected density of capture probes as maximum density of capture probes and initiates the removal of the last added capture probes 710. By removing the last set of capture probes, the system or a system operator can determine the optimal density of capture probes on the test system 712.

Example Flowchart

Figure 8:
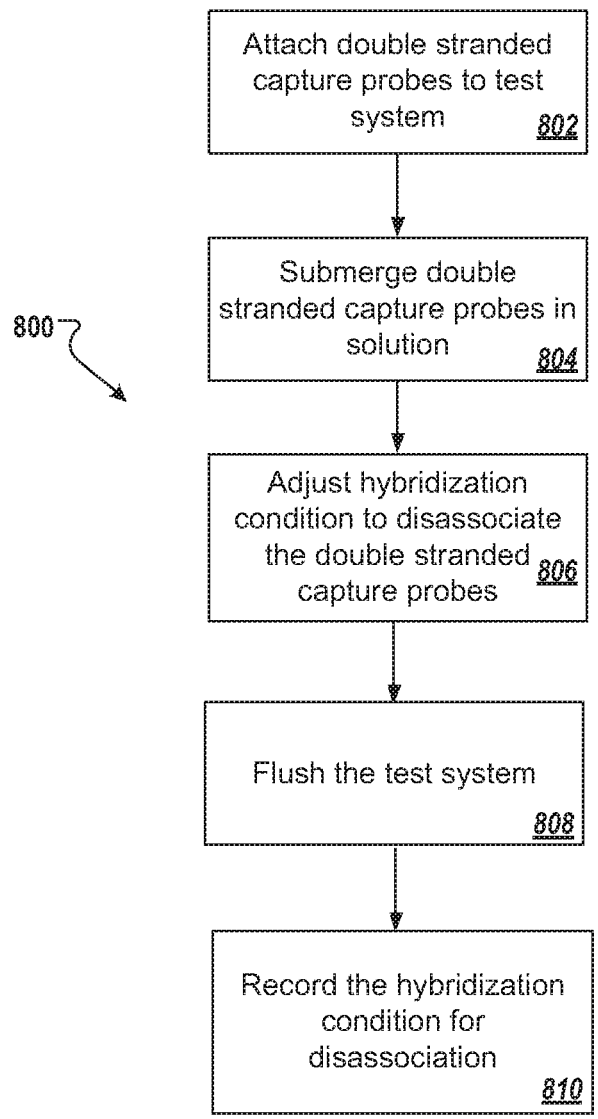
FIG. 8 is a flowchart depicting an example process that can be executed in accordance with implementations of the present disclosure.

FIG. 8 is a flowchart depicting an example process 800 that can be executed in accordance with implementations of the present disclosure. In some examples, the example process 800 can include operations that are performed by a user of the system or by one or more components of the systems described with reference to FIGS. 1-5. The example process 800 can be an example protocol for calibrating the test system prior to exposing the capture probes to the test nucleic acids.

One or more double stranded nucleic acid capture probes can be attached to a hybridization surface of the test system 802. The double stranded nucleic acid capture probes can include a single or multiple types of nucleobases. The double stranded nucleic acid capture probes can be submerged in a buffer solution 804. The buffer solution can have a particular ionic strength.

One or more hybridization conditions of the test system can be progressively adjusted until a degree of disassociation of the double stranded nucleic acid capture probes is reached 806. In some implementations, the hybridization conditions can be adjusted until a significant majority or all double stranded nucleic acid capture probes are disassociated. In some implementations, the hybridization conditions can be adjusted until a particular type of double stranded nucleic acid capture probes are disassociated. After the disassociation of the double stranded nucleic acid capture probes, the solution contains single stranded nucleic acid and single stranded nucleic acid capture probes remain attached to the surface.

The solution from the test system can be flushed out, the test system single stranded nucleic acid capture probes remaining attached to the surface 808. In some implementations, the test system is flushed with buffer solution free of nucleic acids, after each disassociation to prevent interference between the single stranded nucleic acids in the solution and single stranded nucleic acid capture probes that remained attached to the surface of the test system. The hybridization condition at which the degree of disassociation of the double stranded nucleic acid capture probes is reached is recorded 810. In some implementations, the step of 810 occurs before the step of 808. In some implementations, the calibration process 800 includes an accurate measurement of a melting temperature that takes into account the nucleic acid type, the ionic strength of the buffer solution, the thermo-gradients across the attachment surfaces, the temperature difference between the temperature sensor, the test system and other conditions that can influence the hybridization.

In an example implementation of the calibration process 800, a test system can include three attachment surfaces. Each of the attachment surfaces can include a particular type of double stranded nucleic acid capture probes. Each of the double stranded nucleic acid capture probes can have a particular melting point. The melting temperature of any double stranded nucleic acid is the temperature at which half of the hybrid dissociates into two complementary single stranded nucleic acid. The melting temperature can be largely determined by the number of bases and the CG content. The melting temperature for two or more closely-related double stranded nucleic acid sequences can be nearly identical. In addition, the difference in melting temperature between a perfectly matched double stranded nucleic acid allele and a closely-related, mismatched double stranded nucleic acid sequence can decrease with increasing length. The difference in melting temperature, between a perfectly matched allele and an allele with a single base difference for an allele over 200 bases long, can be less than 1° C.

Within the context example, the first type of double stranded nucleic acids can disassociate at temperature $T_1$, the second type of double stranded nucleic acids can disassociate at temperature $T_2$ and the third type of double stranded nucleic acids can disassociate at temperature $T_3$. After each melting temperature was recorded, the hybridization surface can be flushed with buffer solution free of nucleic acids. Flushing the hybridization surface can prevent the interference of single stranded nucleic acids released from one attachment surface with single stranded capture probes attached to a different surface. After the melting temperature for each type of double stranded nucleic acids capture probes was identified, the single stranded nucleic acids capture probes can be identified as described with reference to FIG. 6.

Example Flowchart

Figure 9:
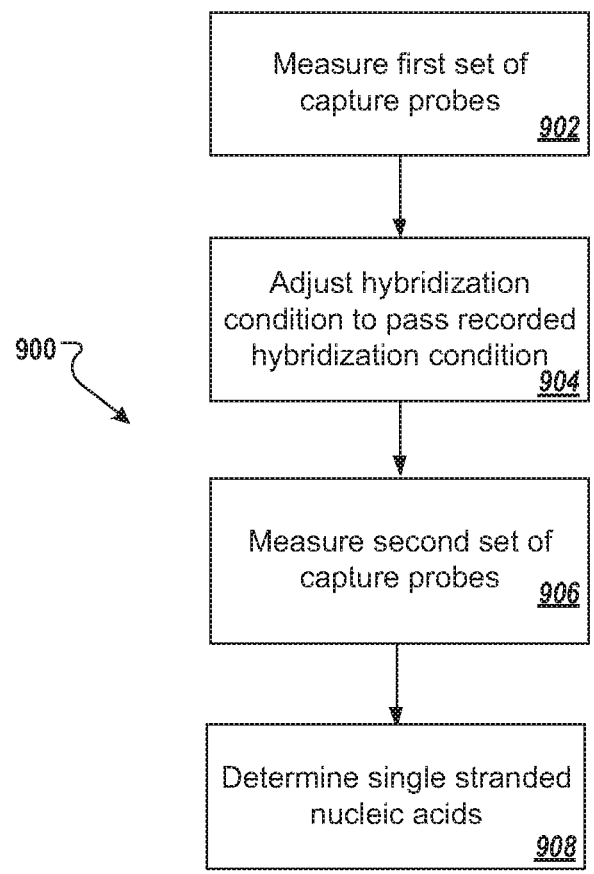
FIG. 9 is a flowchart depicting an example process that can be executed in accordance with implementations of the present disclosure.

FIG. 9 is a flowchart depicting an example process 900 that can be executed in accordance with implementations of the present disclosure. In some examples, the example process 900 can include operations that are performed by a user of the system or by one or more components of the systems described with reference to FIGS. 1-5. The example process 900 is an example protocol for compensating for substances other than the target nucleic acids landing on the attachment surface.

A first set of nucleic acid capture probes attached to the surface of the test system can be measured 902. One or more hybridization conditions of the test system can be progressively adjusted until the recorded hybridization condition is passed 904. A second set of nucleic acid capture probes attached to the surface of the test system is measured 906. The second set of nucleic acid capture probes can include the first set of nucleic acid capture probes at a different time, corresponding to different hybridization conditions. The measurement data from the second set of nucleic acid capture probes with measurement data from the first set of nucleic acid capture probes are used to determine changes to the single stranded nucleic acid capture probes 908.

In an example implementation of the compensation process 900, the first set of nucleic acid capture probes attached to the surface of the test system includes double stranded nucleic acid capture probes. The adjustment of the hybridization conditions can include heating the attachment surface higher than the melting temperature of the capture probes on the attachment surface. The second set of nucleic acid capture probes can include single stranded nucleic acid capture probes. The single stranded capture probe measurement can be subtracted from the double stranded nucleic acid capture probes measurement to determine the amount of single stranded target bound to capture probes on the attachment surface.

In another example implementation of the compensation process 900, the first set of nucleic acid capture probes attached to the surface of the test system includes single stranded nucleic acid capture probes. The adjustment of the hybridization conditions can include cooling the attachment surface bellow the melting temperature of the capture probes on the attachment surface. The second set of nucleic acid capture probes can include double stranded nucleic acid capture probes. The single stranded capture probe measurement can be subtracted from the double stranded nucleic acid capture probes measurement to determine the amount of single stranded target bound to capture probes on the attachment surface.

In some implementations, the compensation process 900 can be applied to more than two nucleic acid types and the melting temperatures corresponding to each type of nucleic acid can be stored in a database (e.g., as a table). In some implementations, a plurality of statistical tools (e.g., interpolation, filters, etc.) can be used to decrease the sample size and to improve the accuracy of the compensation process 900. A table of melting temperatures for the nucleic acids of interest can be derived for each test system.

In some implementations, the compensation process 900 can be performed after the calibration process 800, described with reference to FIG. 8. In some implementations, the melting temperature can depend on the test system. The compensation process 900 and the calibration process 800 can be used to eliminate the dependency to the test system, by providing a reference point for particular target nucleic acids.

The logic flows depicted in FIGS. 6-8 do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

Example Flowchart

Figure 10:
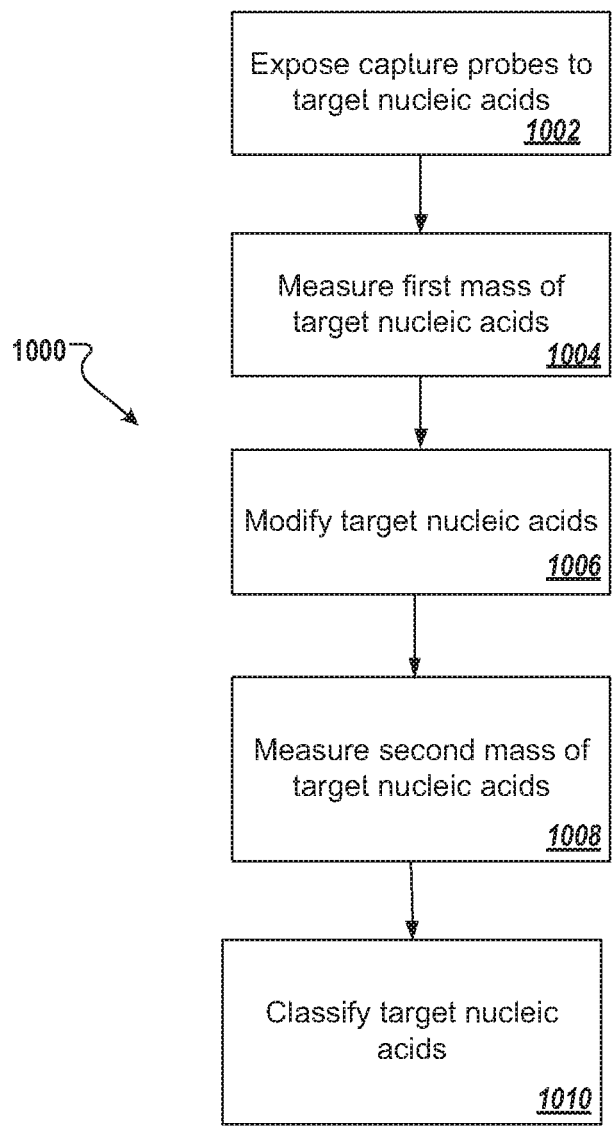
FIG. 10 is a flowchart depicting an example process that can be executed in accordance with implementations of the present disclosure.

FIG. 10 is a flowchart depicting an example process 1000 that can be executed in accordance with implementations of the present disclosure. In some examples, the example process 1000 can include operations that are performed by a user of the system or by one or more components of the systems described with reference to FIGS. 1-5. The example process 1000 is an example test nucleic acids classification protocol with output that can be stored in an internal or external memory. In some implementations, classifying a test nucleic acid includes differentiating a target nucleic acid from a non-target nucleic acid. In case a test nucleic acid is classified as a target, the test nucleic acid can be identified.

One or more capture probes are exposed to test nucleic acids in a test system, the one or more capture probes being attached to a surface 1002. The test nucleic acids can include a target nucleic acid with a particular mass that is complementary to a capture probe located at a first location and other target nucleic acids with different masses that are complementary to capture probes, attached to other locations on the surface. In some implementations, the test system includes a detector configured to measure a mass of an object on at least one surface of the detector. The detector can be a resonator system. The captures probes can be attached to the surface of the resonator system, which can measure the first mass of the capture probes hybridized with the target nucleic acids 10004. In some implementations, the target nucleic acid can be very light, the hybridization of the capture probes with the target nucleic acids resulting into a change in mass below the resolution of the detector.

The target nucleic acid is modified 1006. The modified target nucleic acid is characterized by a second mass. In some implementations, a mass reporter can be attached to the target nuclei acid, as described with reference to FIGS. 5C and 5D. The mass reporter can be a heavy nucleic acid extension. The modification of the target nucleic acid can be based on covalent or non-covalent binding. An example of a covalent modification of mass of the target nucleic acids can include a chemical reaction.

An example of a covalent modification of mass of the target nucleic acids can include incorporation of biotin by the use of a byotinilated primer during PCR. The biotinylated nucleic acid can bind a biotin-binding protein that contains or more biotin binding sites. The biotin-binding protein can contain two or more biotin binding sites. The secondary compounds, such as biotinylated polymeric beads, antibodies, dendrimers, macromolecules and polymers can bind with the target nucleic acid increasing its mass to enable accurate mass measurement. The nucleic acid extension can hybridize to complementary single or double stranded nucleic acids in the test medium resulting in increased mass. The target nucleic acid binds to a nucleic acid enzyme or nucleic acid apoenzyme without the addition of cofactors enabling a controlled increase of mass. A hybridized single or double stranded nucleic acid extension can have additional unpaired regions that can be used for further extensions resulting in increase of mass. In some examples, a hybridized single or double stranded nucleic acid extension can inhibit the addition of further extensions.

In some implementations, the target nucleic acids can be modified by compounds or functional groups that interact with large molecules with high affinity, thereby increasing mass at a particular location of the test system. The compounds can be high affinity antigen-antibody pairs such as digoxigenin and anti-digoxigenin antibodies. The functional groups can include thiols, dithiols, sulfides, active esters, amines, hydrazides, azides, ynes, diynes, and acrydites The detector measures the second mass of the capture probes hybridized with the extended target nucleic acids 1008. The detector can measure the change in mass at each location on its surface, each location including a particular type of capture probes. In some implementations, after the second mass of nucleic acids is measured, a nucleic acid strand can be removed from the target nucleic acid. The removed nucleic acid strand can be the entire mass reporter initially added or it can be a part of the mass reporter initially added. For example, the removed nucleic acid strand can be a functional group from the first added mass reporter that inhibited further extension of the nucleic acid strand. A series of mass addition, mass measurement and mass removal can be used to classify one or more target nucleic acids.

In some implementations, the process 1000 can be repeated multiple times with different mass reporters for identification of a plurality of target nucleic acids. The process 1000 can be combined with any of the processes previously described with reference to FIGS. 6-9. For example, process 600, described with reference to FIG. 6, can be performed in combination with process 1000 to increase the accuracy of the detection system and decrease the quantity of nucleic acid.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A method for classifying a target nucleic acid, the method comprising:
  exposing, in a test system, a plurality of capture probes to the target nucleic acid, the test system comprising a conditioning system, a hybridization surface, and a processor, the conditioning system being configured to apply an adjustable conditioning parameter at the plurality of capture probes, the plurality of capture probes being attached to the hybridization surface and at least two of the plurality of capture probes having different abilities to hybridize to the target nucleic acid;
  establishing a first hybridization condition by adjusting the adjustable conditioning parameter in the conditioning system to a first value;
  determining, by the processor, a first degree of hybridization of the plurality of capture probes with the target nucleic acid under the first hybridization condition, the first degree of hybridization comprising at least one of a first association rate and a first dissociation rate of the target nucleic acid from each capture probe under the first hybridization condition;
  establishing a second hybridization condition by adjusting the adjustable conditioning parameter in the conditioning system to a second value;
  determining, by the processor, a second degree of hybridization of the plurality of capture probes with the target nucleic acid under the second hybridization condition, the second degree of hybridization comprising at least one of a second association rate and a second dissociation rate of the target nucleic acid from each capture probe under the second hybridization condition; and
  classifying, by the processor, the target nucleic acid by determining differences between the first degree of hybridization and the second degree of hybridization with respect to each of the plurality of capture probes and comparing the differences to a model of differences of degrees of hybridization of known nucleic acids.

2. The method of claim 1, wherein:
  the test system comprises one or more sensors on the surface configured to measure hybridization of the plurality of capture probes with the target nucleic acid.

3. The method of claim 2, wherein:
  the one or more sensors is a resonator array configured to measure a mass of an object on at least one surface of the resonator array;

the plurality of captures probes are attached to the surface of the resonator array; and determining the first and second degrees of hybridization of the plurality of capture probes with the target nucleic acid comprises measuring the mass on the surface of the resonator array.

4. The method of claim 1, wherein:

exposing the plurality of capture probes to the target nucleic acid comprises contacting the plurality of capture probes with a solution containing the target nucleic acid;

establishing the first hybridization condition comprises adjusting a temperature of the solution to a first temperature; and establishing the second hybridization condition comprises adjusting the temperature of the solution to a second temperature.

5. The method of claim 1, wherein the first hybridization condition is selected to minimize hybridization between a target nucleic acid and the plurality of capture probes, and wherein the second hybridization condition is selected to favor hybridization between the target nucleic acid and the plurality of capture probes.

6. The method of claim 1, further comprises:

based on establishing the first hybridization condition, progressively adjusting the adjustable conditioning parameter in the conditioning system to favor hybridization between a target nucleic acid and the plurality of capture probes;

after each adjustment, determining a degree of hybridization of the plurality of capture probes with the target nucleic acid; and continuing to adjust the adjustable conditioning parameter in the conditioning system until the degree of hybridization reaches a threshold degree of hybridization.

7. The method of claim 1, wherein the test system comprises first capture probes at a first location and one or more second capture probes at a second location, and the method further comprising:

progressively adjusting the adjustable conditioning parameter in the conditioning system;

after each adjustment, determining a respective degree of hybridization for each of the first and second locations; and determining whether the degree of hybridization at the first location reaches a threshold degree of hybridization prior to or after the degree of hybridization at the second location reaches the threshold degree of hybridization.

8. The method of claim 1, further comprising calibrating the test system prior to exposing the plurality of capture probes to the target nucleic acid, by performing operations comprising:

attaching one or more double stranded nucleic acid capture probes to a surface of the test system;

contacting the one or more double stranded nucleic acid capture probes with a solution;

progressively adjusting one or more hybridization conditions of the test system until a degree of dissociation of the double stranded nucleic acid capture probes is reached, so that the solution contains single stranded nucleic acid and single stranded nucleic acid capture probes remain on the surface; recording the one or more hybridization conditions at which the degree of dissociation of a first double stranded nucleic acid capture probes is reached, generating a single stranded nucleic acid; and removing the single stranded nucleic acid from the test system.

9. The method of claim 8, wherein calibrating the test system prior to exposing the plurality of capture probes to the target nucleic acid, further comprises:

measuring a first set of nucleic acid capture probes attached to the surface of the test system;

progressively adjusting the one or more hybridization conditions of the test system until a recorded hybridization condition is passed;

measuring a second set of nucleic acid capture probes attached to the surface of the test system; and determining changes to the single stranded nucleic acid capture probes based on the first set of nucleic acid capture probes and the second set of nucleic acid capture probes.

10. The method of claim 1, wherein the difference indicates whether a matched or a mis-matched hybridization occurred for each of the plurality of capture probes.

11. A method for classifying a target nucleic acid, the method comprising:

exposing, in a test system, a plurality of capture probes to the target nucleic acid, the test system comprising a conditioning system, a hybridization surface, and a processor, the conditioning system being configured to apply one or more adjustable conditioning parameters at the plurality of capture probes, the plurality of capture probes being attached to the hybridization surface and at least two of the plurality of capture probes having different abilities to hybridize to the target nucleic acid;

establishing a first hybridization condition by adjusting one or more conditioning parameters in the conditioning system to a first value;

determining, by the processor, a first degree of hybridization of the plurality of capture probes with the target nucleic acid under the first hybridization condition, the first degree of hybridization comprising at least one of a first association rate and a first dissociation rate of the target nucleic acid from each capture probe under the first hybridization condition;

establishing a second hybridization condition by adjusting the one or more conditioning parameters in the conditioning system to a second value;

determining, by the processor, a second degree of hybridization of the plurality of capture probes with the target nucleic acid under the second hybridization condition, the second degree of hybridization comprising at least one of a second association rate and a second dissociation rate of the target nucleic acid from each capture probe under the second hybridization condition; and classifying, by the processor, the target nucleic acid by generating a sequence of hybridization degrees with respect to each of the plurality of capture probes based on the first degree of hybridization and the second degree of hybridization and comparing the sequence of hybridization degrees to a model sequence of hybridization degrees of a known nucleic acid comprising the melting temperatures for each capture probe.

12. The method of claim 11, wherein at least one of the plurality of capture probes is a perfect complementary capture probe for the known nucleic acid.

13. The method of claim 11, wherein none of capture probes is a perfect complementary capture probe for the target nucleic acid.

14. A method for classifying a target nucleic acid, the method comprising:

exposing, in a test system, a plurality of capture probes to the target nucleic acid, the test system comprising a conditioning system, a hybridization surface, and a processor, the conditioning system being configured to apply an adjustable conditioning parameter at the plurality of capture probes, the plurality of capture probes being attached to the hybridization surface and at least two of the plurality of capture probes having different abilities to hybridize to the target nucleic acid;

progressively adjusting the adjustable conditioning parameter in the conditioning system across a range of values;

for each respective capture probe, recording a respective value of the adjustable conditioning parameter at which the respective capture probe reaches a predetermined degree of hybridization with the target nucleic acid, the plurality of capture probes thus providing a sequence of conditioning parameter values comprised of the respective value for each respective capture probe; and classifying, by the processor, the target nucleic acid as one of a plurality of test nucleic acids by comparing the sequence of conditioning parameter values to a plurality of test sequences, each test sequence comprising a sequence of conditioning values for a different test nucleic acid from the plurality of test nucleic acids.

15. The method of claim 14, wherein none of capture probes is a perfect complementary capture probe for the target nucleic acid.

* * * * *